US009579200B2

(12) United States Patent
Lederman et al.

(10) Patent No.: US 9,579,200 B2
(45) Date of Patent: Feb. 28, 2017

(54) METHODS AND DEVICES FOR TRANSCATHETER CERCLAGE ANNULOPLASTY

(75) Inventors: Robert J. Lederman, Chevy Chase, MD (US); Ozgur Kocaturk, Rockville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 431 days.

(21) Appl. No.: 13/824,198

(22) PCT Filed: Sep. 15, 2011

(86) PCT No.: PCT/US2011/051748
§ 371 (c)(1),
(2), (4) Date: May 1, 2013

(87) PCT Pub. No.: WO2012/037341
PCT Pub. Date: Mar. 22, 2012

(65) Prior Publication Data
US 2013/0211510 A1    Aug. 15, 2013

Related U.S. Application Data

(60) Provisional application No. 61/383,061, filed on Sep. 15, 2010.

(51) Int. Cl.
*A61B 17/24* (2006.01)
*A61F 2/24* (2006.01)
(Continued)

(52) U.S. Cl.
CPC ...... *A61F 2/2451* (2013.01); *A61B 17/00234* (2013.01); *A61B 17/221* (2013.01);
(Continued)

(58) Field of Classification Search
CPC ........... A61M 25/0147; A61M 25/0133; A61F 2/2418; A61F 2/2427; A61F 2/2466
(Continued)

(56) References Cited

U.S. PATENT DOCUMENTS

| 3,572,325 | A | * | 3/1971 | Bazell et al. ................. 600/141 |
| 5,311,866 | A | * | 5/1994 | Kagan et al. ................. 600/374 |
| 5,345,936 | A | * | 9/1994 | Pomeranz et al. ............ 600/374 |
| 2005/0038447 | A1 | | 2/2005 | Huffmaster |
| 2005/0256521 | A1 | * | 11/2005 | Kozel .................. A61B 5/0422 606/41 |
| 2007/0185500 | A1 | | 8/2007 | Martin et al. |
| 2007/0249901 | A1 | * | 10/2007 | Ohline et al. ................. 600/117 |
| 2008/0004534 | A1 | * | 1/2008 | Gelbart .................. A61B 5/028 600/508 |
| 2008/0058800 | A1 | * | 3/2008 | Collins et al. .................. 606/41 |

(Continued)

FOREIGN PATENT DOCUMENTS

| WO | WO-94/06357 A1 | 3/1994 |
| WO | WO-99/48429 A1 | 9/1999 |

(Continued)

OTHER PUBLICATIONS

International Search Report from PCT/US2011/051748, mailed on Nov. 24, 2011.

*Primary Examiner* — Todd E Manahan
*Assistant Examiner* — Erich Herbermann
(74) *Attorney, Agent, or Firm* — Bryan D. Zerhusen; Locke Lord LLP

(57) ABSTRACT

Devices, apparatus, and methods for catheter-based repair of cardiac valves, including transcatheter-mitral-valve-cerclage annuloplasty and transcatheter-mitral-valve reapposition. In particular, a target and capture device is provided for guiding a cerclage traversal catheter system through a cerclage trajectory, particularly through a reentry site of the cerclage trajectory. The target and capture device provides the user with a target through which the cerclage traversal catheter system must be guided, particularly under imaging guidance, so as to properly traverse the cerclage trajectory at any desired location, particularly at a reentry site. The target and capture device can, further, ensnare and externalize the cerclage traversal catheter system.

16 Claims, 13 Drawing Sheets

(51) Int. Cl.
*A61B 17/00* (2006.01)
*A61B 17/221* (2006.01)
A61B 17/02 (2006.01)
A61B 17/22 (2006.01)

(52) U.S. Cl.
CPC .. *A61F 2/2466* (2013.01); *A61B 2017/00243* (2013.01); *A61B 2017/00314* (2013.01); *A61B 2017/00327* (2013.01); *A61B 2017/0237* (2013.01); *A61B 2017/22035* (2013.01); *A61B 2090/3966* (2016.02)

(58) Field of Classification Search
USPC ................ 604/525; 623/1.11–1.15; 600/113, 600/127–128
See application file for complete search history.

(56) References Cited

U.S. PATENT DOCUMENTS

| | | | |
|---|---|---|---|
| 2008/0228171 | A1 | 9/2008 | Kugler et al. |
| 2008/0249397 | A1* | 10/2008 | Kapadia ........................ 600/424 |
| 2008/0306499 | A1 | 12/2008 | Katoh et al. |
| 2009/0171274 | A1* | 7/2009 | Harlev et al. .............. 604/95.04 |

FOREIGN PATENT DOCUMENTS

| | | |
|---|---|---|
| WO | WO-2006/105008 A1 | 10/2006 |
| WO | WO-2008/070262 A2 | 6/2008 |

* cited by examiner

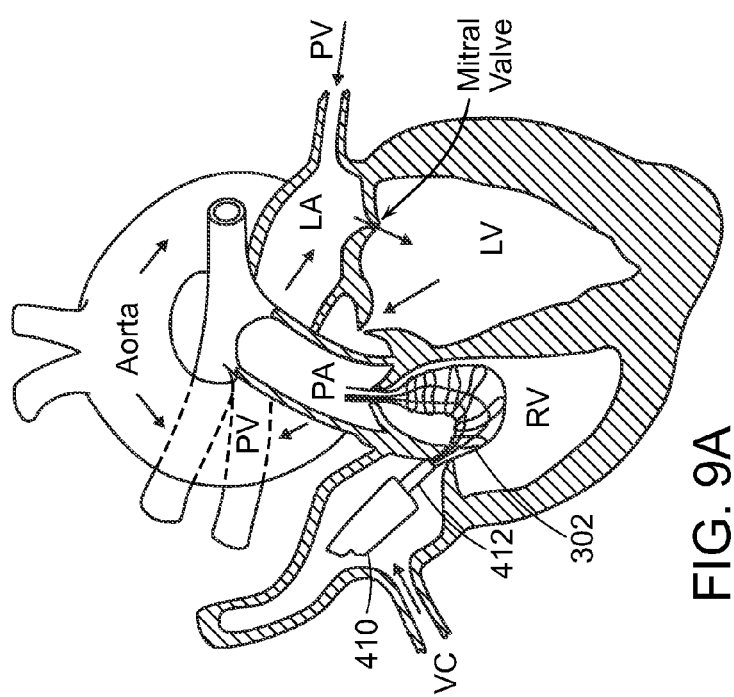
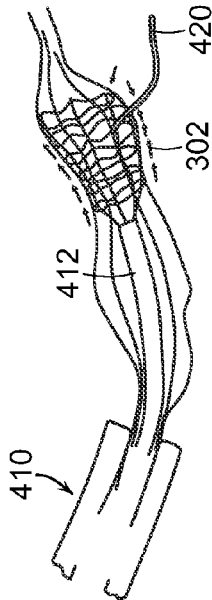
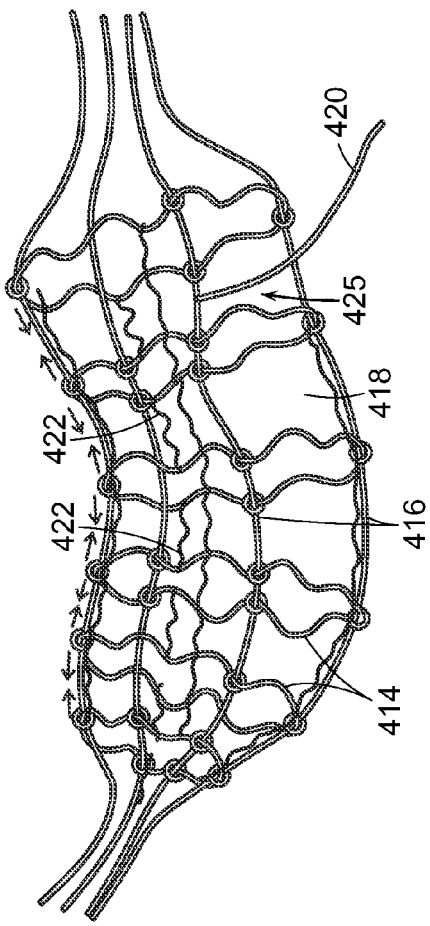
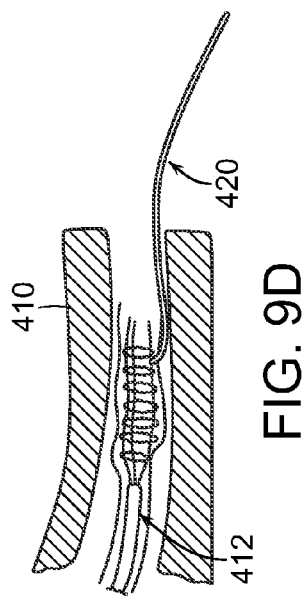

METHODS AND DEVICES FOR TRANSCATHETER CERCLAGE ANNULOPLASTY

The present application is a national phase application pursuant to 35 U.S.C. §§371 of International Application No. PCT/US2011/051748, filed Sep. 15, 2011, which claims the benefit of U.S. provisional application No. 61/383,061 filed Sep. 15, 2010, both of which are incorporated herein by reference in their entireties.

GOVERNMENT SUPPORT

This invention was funded by the National Institute of Health. The United States Government has certain rights in this invention.

FIELD OF INVENTION

The present invention generally relates to techniques and devices for cardiovascular valve repair, particularly annuloplasty techniques and devices in which tensioning elements are positioned to treat regurgitation of the mitral valve or tricuspid valve.

BACKGROUND

In the mammalian heart, the tricuspid valve separates the right atrium and right ventricle and prevents backflow of blood from the right ventricle into the right atrium during contraction. The left atrium and left ventricle are separated by the mitral valve, which, similar to the tricuspid valve, prevents backflow of blood into the left atrium when the left ventricle contracts.

Regurgitation (leakage) of the mitral valve or tricuspid valve can result from many different causes, and can cause heart irregularities, such as an irregular heart rhythm, and itself can cause inexorable deterioration in heart-muscle function. Such deterioration can be associated with functional impairment, congestive heart failure and significant pain, suffering, lessening of the quality of life, or even death. Mitral valve regurgitation ("MR") is broadly categorized as either organic or secondary (i.e. functional). With organic MR, there is a primary structural abnormality of the mitral valve resulting in improper coaptation of the valve. The most common causes of organic MR include degenerative disease, rheumatic valve disease, endocarditis with leaflet destruction, and congenital mitral valve disease. With secondary MR, the leaflet structure is largely preserved and regurgitation is caused by a dilated annulus and/or subvalvular traction impairing leaflet apposition.

Pharmacologic treatments for valvular regurgitation generally include diuretics and vasodilators. These medicines, however, have not been shown to alter the natural progression of cardiac dysfunction associated with regurgitant valves.

Cardiac resynchronization therapy (biventricular pacing) has value as a non-surgical option in "functional" or secondary mitral valve regurgitation.

Surgical options for correcting defects in the heart valves include repair or replacement of a valve, but these surgical options require open-heart surgery, which generally requires stopping the heart and cardiopulmonary bypass. Recovery from open-heart surgery can be very lengthy and painful, or even debilitating, since open-heart surgery requires pulling apart the ribs to expose the heart in the chest cavity. Cardiopulmonary bypass itself is associated with comorbidity, including cognitive decline. Additionally, open-heart surgery carries the risk of death, stroke, infection, phrenic-nerve injury, chronic-pain syndrome, venous thromboembolism, and other complications. In fact, a number of patients suffering heart-valve defects cannot undergo surgical-valve treatment because they are too weak or physiologically vulnerable to risk the operation. A still larger proportion of patients have mitral-valve regurgitation that is significant, but not sufficiently so to warrant the morbidity and mortality risk of cardiac surgery.

Percutaneous approaches to valve repair have been developed to reduce the clinical disadvantages of the open-heart procedures. In some percutaneous techniques, a prosthesis is advanced in a catheter through the subject's vasculature to the vicinity of the mitral valve. These percutaneous techniques are attractive alternatives to conventional surgical treatment because they do not require open heart surgery or extracorporeal circulation, and can be used in a closed chest and beating heart. The treatment is potentially less morbid and can be applied to a wider range of patients including those with less severe valvular dysfunction.

Examples of percutaneous valve repair procedures include coronary-sinus shortening devices, transcameral fixtures, endoventricular annular plication, and direct leaflet stapling. Coronary sinus annuloplasty techniques have been disclosed, for example, in U.S. Pat. Nos. 6,402,781 and 7,090,695. However, these techniques have shown only limited success in establishing circumferential tension that characterizes effective surgical ring annuloplasty. For example, in mitral valve repair, the sinus-shortening devices have induced only local shortening across the mitral commissures but do not adequately reduce the septal-lateral separation that characterizes functional mitral valve regurgitation. The leaflet procedures have not been able to reduce annular dilation and they can also impair the normal dynamic line of mitral valve coaption that accommodates a range of volumes and inotropic states.

A more recent improvement of percutaneous annuloplasty is percutaneous cerclage annuloplasty or coronary sinus transcatheter-mitral-valve cerclage annuloplasty, which is disclosed, for example, in U.S. Published Patent Application Nos. 2005/0216039 and 2010/0049314. This technique involves the introduction of tensioning material around the mitral-valve annulus using a secondary catheter, such as a steerable guide wire or canalization catheter. Access to the area around the mitral-valve annulus can be accomplished using a number of different percutaneous approaches, including access from and through the coronary sinus. For example, a continuous strand of tensioning material such as a ligature is applied around the mitral-valve annulus along a pathway that includes an extraanotomic portion. For example, the tensioning material can traverse a region between the anterobasal-most portion of the coronary sinus and the coronary-sinus ostium. In another approach, a tensioning material is applied across the atrial aspect of the mitral valve from the posterolateral aspect to the anterior aspect of the coronary sinus, or from the septal aspect to the lateral aspect of the mitral-valve annulus. By such cerclage techniques, the mitral annular cross-sectional area is reduced, including a reduction in septal-lateral wall separation, thereby intrinsically reapposing the line of coaptation of the mitral valve. During such techniques, the tensioning material can be placed with the assistance of imaging technologies that may include X-ray fluoroscopy, magnetic resonance imaging, intracavitary or external ultrasound, electroanatomic mapping, X-ray computed tomography or a combination (fusion) of any of these imaging technologies.

While percutaneous cerclage annuloplasty is a promising technique for valve repair, enhancing valve leaflet coaptation, and treating valve regurgitation, the procedure is technically demanding and requires great skill and precision in positioning the tensioning system to provide the proper plane of cerclage. Further, entrapment of tricuspid valve subvalvular structures, such as trabeculae or chorda tendinea or of ventricular structures such as the moderator band and non-valvar trabeculae, is an important limiting adverse consequence of the cerclage procedure that requires great skill, effort and prolonged procedures to avert. Entrapment occurs when a cerclage traversal catheter system undermines a trabecular or other subvalvar element while it passes from an intramyocardial trajectory into the right ventricular cavity. In the event that such entrapment is not averted, the subvalvar or trabecular structures may become entrapped or transsected, and the tricuspid valve or right ventricle may be irreversibly damaged causing procedural failure and serious adverse consequences. Therefore, a need exists for improved techniques and devices that facilitate proper positioning of the tensioning system during such demanding and complex cerclage procedures and, further, which can prevent trabecular entrapment

SUMMARY OF THE DISCLOSURE

The present invention features methods, apparatus and devices for repairing cardiac valves in a patient and, particularly to such methods, apparatus and devices for minimally invasive and percutaneous procedures for repairing damaged or malfunctioning cardiac valves in a patient. In particular, methods, apparatus and devices of the present invention facilitate mitral-valve cerclage annuloplasty. Specifically, a tensioning material is provided in a target cerclage trajectory using a cerclage traversal catheter system. In accordance with the present invention, a target and capture device is provided for properly guiding and capturing the cerclage traversal catheter system as it follows the trajectory and reenters the right heart chamber as it passes through and emerges from the septal myocardial tissue.

In an exemplary embodiment, there is featured a method for performing a mitral-valve cerclage annuloplasty by introducing a target and capture device into the vasculature of a patient, positioning the target and capture device at a desired location of a cerclage trajectory, and introducing a tensioning system via a cerclage traversal catheter system through the cerclage trajectory, wherein the target and capture device provides a target for guiding the cerclage traversal catheter system through the desired trajectory location, and wherein the target and capture device captures and/or ensnares the cerclage traversal catheter system as or after the cerclage traversal catheter system passes through the desired trajectory location.

Aspects in accordance with this embodiment can include the following features. The cerclage trajectory can include the coronary sinus, great cardiac vein, and basal septal perforator vein, followed by traversing a segment of the interventricular myocardial septum to reenter the right ventricle or right atrium ("reentry site"), and the target and capture device can be positioned at the desired reentry site so as to guide the cerclage traversal catheter system properly through the reentry site. The target and capture device can, further, capture or ensnare the cerclage traversal catheter system as or after the cerclage traversal catheter system passes through the reentry site. The target and capture device can be provided with at least one opening, wherein the opening is a target through which the cerclage traversal catheter system is guided into the reentry site and, further, the cerclage traversal catheter system is captured or ensnared in the opening. The target and capture device can comprise a shaft or elongate member with a distal opening and/or loop. The target and capture device can comprise a mesh. At least a portion of the target and capture device can be imageable under the specified imaging guidance modality, including X-ray fluoroscopy, echocardiography, magnetic resonance imaging, and electroanatomic positioning. For example, at least the portion of the device surrounding the opening, or at least a portion of the loop, etc. can be imageable. As such, the opening or loop can be properly positioned at the desired reentry site with the assistance of imaging techniques, and the cerclage traversal catheter system can further be directed into and/or through the opening or loop which thereby serves as a target. In yet further embodiments, the target and capture device is configured to conform to the curvature of the right ventricle. For example, the target and capture device can comprise a loop or mesh configured to conform to the curvature of the right ventricle and, further, so as to be torqued to abut the tissue of the right ventricle so as to further ensure that the cerclage traversal catheter system passes through the desired reentry site and so as to reduce the likelihood of trabecular entrapment. The target and capture device can be configured, arranged and/or positioned so as to displace desired structures so as to prevent entrapment and/or injury to such structures as the cerclage traversal catheter system traverses the cerclage trajectory. The target and capture device can be configured, arranged and/or positioned so as to retrieve the cerclage traversal catheter system at the desired reentry site, particularly after the cerclage traversal catheter system has been captured or ensnared by the target and capture device.

In an exemplary embodiment, there is featured a method for performing transcatheter cerclage annuloplasty to repair a valve in a patient by inserting a cerclage traversal catheter system into the vasculature of a patient and positioning a target and capture device at a desired reentry site in the right ventricle. The target and capture device can comprises a loop having an opening or a mesh having a plurality of openings, and the loop or mesh can be at least partially imageable so as to provide an imageable target at the desired reentry site. The cerclage trajectory is traversed using the cerclage traversal catheter system, the imageable target is imaged, and the cerclage traversal catheter system is guided through the imageable target positioned at the desired reentry site. The cerclage traversal catheter system is exchanged with a tensioning element and tension is applied on the tensioning element. The step of positioning a target and capture device at the desired reentry site in the right ventricle can comprise positioning the target or capture device while imaging the loop or mesh. The step of positioning a target and capture device can comprise positioning the loop or mesh so as to conform to the curvature of the right ventricle. Positioning the target and capture device can further comprise displacing vascular structures with the target and capture device from the luminal aspect of the chamber to the endocardial aspect of the chamber to prevent entrapment or injury to the vascular structures. The target and capture device an be positioned to displace right ventricular trabecular and tricuspid subvalvular structures away from the central right heart cavity against the right ventricular endocardial surface. A single opening of the mesh can be fabricated of imaging material, and the single opening can be positioned at the desired reentry site. The cerclage traversal catheter system can further be ensnared the by the target and capture device after the cerclage traversal catheter system is guided through the imageable target. The cerclage traversal catheter system can further be retrieved using the target and capture device after the cerclage traversal catheter system is guided through the imageable target. The target and capture device can comprise a loop that can be manipulated in size, and the method can further comprise manipulating the size of the loop so as to ensnare the cerclage traversal catheter system. The mesh can be expandable and collapsible, wherein the mesh can expand so as to conform to the curvature of the right ventricle when it is positioned, and the method can further comprises collapsing the mesh so as to ensnare the cerclage traversal catheter system.

In another exemplary embodiment, there is featured a method for performing transcatheter cerclage annuloplasty to repair a valve in a patient by inserting a cerclage traversal catheter system into the vasculature of a patient, positioning a first target and capture device comprising a mesh having a plurality of openings within the right ventricle, displacing trabecular structures with the first target and capture device, and positioning a second target and capture device comprising a loop at a desired reentry site in the right ventricle. The cerclage trajectory is traversed using the cerclage traversal catheter system, the cerclage traversal catheter system is guided the through the loop positioned at the desired reentry site, the cerclage traversal catheter system is exchanged with a tensioning element, and tension is applied on the tensioning element. Aspects in accordance with this embodiment can include the following features. The cerclage traversal catheter system can be further ensnared the within the loop after the cerclage traversal catheter system is guided through the loop. The cerclage traversal catheter system can be retrieved using the loop after the cerclage traversal catheter system is guided through the loop.

According to another embodiment of the present invention, there is featured a target and capture device for use in performing percutaneous cerclage annuloplasty. In accordance with this aspect, the target and capture device can comprise an elongate member, such as a shaft, having an opening and/or a loop or the like positioned at or near the distal end of the elongate member. The opening and/or loop has or assumes the shape of the right ventricular outflow tract.

Aspects in accordance with this embodiment can include the following features. The opening can be configured so as to be capable of capturing and/or ensnaring a cerclage traversal catheter system during a cerclage procedure. The opening can be configured so as to be adjustable in size such that after the cerclage traversal catheter system has passed therethrough, the opening or loop is adjusted (e.g. made smaller) to capture or ensnare the cerclage traversal catheter system therein. At least a portion of the target and capture device can be imageable, such as at least a portion surrounding the opening. The target and capture device can comprise a loop or opening configured to conform to the curvature of the right ventricle and, further, so as to be torqued to abut the tissue of the right ventricle. The target and capture device can be formed of a shape memory material wherein the loop or portion surrounding the opening has a remembered shape is a shape that conform to the curvature of the right ventricle. The loop can be preformed or formed with a remembered shape that conforms to the inner curvature of the right ventricle to right ventricular outflow tract, thereby conforming to and abutting the interventricular septum reentry site. The loop can be configured, arranged and/or positioned so as to displace desired structures so as to prevent entrapment and/or injury to such structures during a cerclage procedure. The loop can be configured, arranged and/or positioned so as to retrieve the cerclage traversal catheter system during a cerclage procedure, particularly at the desired reentry site after the cerclage traversal catheter system has been captured or ensnared by the target and capture device.

According to another embodiment of the present invention, there is featured a target and capture device for use in performing percutaneous cerclage annuloplasty. In accordance with this aspect, the device comprises an expandable and collapsible mesh configured so as to conform to the curvature of the right ventricle when in its expanded state and configured so as to be insertable through a catheter in a patient's vasculature when collapsed, wherein the expandable and collapsible mesh has an imageable target therein.

Aspects in accordance with this embodiment can include the following features. The imageable target can be an opening or cell in the mesh. The mesh can comprise two or more wire elements that separate when deployed and adjoin when retracted. The mesh can comprise a plurality of criss-crossing wire-like members. The mesh can comprise single or multiple slots cut or molded into a tube, such as an expanding slotted tube having a plurality of slots wherein expansion of the tube provides larger size slots and compression of the tube provides smaller sized slots. The mesh can comprise a plurality of sinusoidal or ring-like elements interconnected with wires that extending along the length of the mesh. The sinusoidal or ring-like elements can be moveable along the wires so as to vary the size of openings in the mesh. The mesh can comprise a plurality of hollow center disc shaped elements interconnected through a plurality of tensioning elements, wherein tension may be independently applied to individual tensioning elements to vary the distance between disk shaped elements and/or the angle between disk-shaped elements. The device can include an expanding element positioned to expand and collapse the mesh. The mesh can be permanently or removably attached, such as at its base or apex, to an expansion mechanism (e.g. a shaft or similar mechanism) for deployment and retrieval, wherein the mechanism is configured to expand the mesh (such as during deployment and positioning at the target), and retract or collapse the mesh (such as during withdrawal of the mesh and/or during capture or ensnaring). The mesh can retract or collapse so as to ensnare or entrap the cerclage traversal catheter system. The mesh can deploy or expand to a shape that conforms to the curvature of the right ventricle. The mesh can be shaped, configured, arranged and/or positioned or expanded to a shape that displaces desired structures so as to prevent entrapment and/or injury to such structures during a cerclage procedure. For example, the mesh can be shaped and/or can deploy or expand to a shape so as to appose the mural tricuspid subvalvular apparatus to the septal myocardial wall. In some embodiments, the mesh can be expanded so as to exert pressure against or displace the trabecular-papillary elements of the tricuspid valve against the right ventricular septal wall. The mesh can be configured so as to displace the valvar chordae and the true and false trabecular muscles against the endocardial border of the right ventricular septum. The mesh can be configured to apply pressure on expansion, thereby displacing the valvar chordae and the true and false trabecular muscles toward the endocardial surface. The mesh can be shaped and/or can deploy or expand to a basket-like U-shape. The mesh can be shaped and/or can deploy or expand to a flat or substantially flat shape. The mesh can be formed of a shape memory material wherein a remembered shape is a shape that conforms to the curvature of the right ventricle. The mesh can be further configured, arranged and/or positioned so as to retrieve the cerclage traversal catheter system during a cerclage procedure, particularly at the desired reentry site after the cerclage traversal catheter system has been captured or ensnared by the target and capture device. The device can further comprise a unipolar or bipolar electrode set for determining the position of the target and capture device in relation to functional electrophysiological fiducial markers.

According to yet another aspect of the invention, there is featured an apparatus for performing percutaneous cerclage annuloplasty comprising a target and capture device for use in combination with a cerclage traversal catheter system.

Aspects in accordance with this embodiment can include the following features. The cerclage traversal catheter system can be configured for traversing a desired cerclage trajectory and reentering the right ventricle or right atrium, and the target and capture device can be configured for positioning at the desired reentry site. The target and capture device can be configured and shaped to provide a target for the cerclage traversal catheter system as the cerclage traversal catheter system reenters the right ventricle or right atrium. The target and capture device can be configured and shaped to capture and/or ensnare the cerclage traversal catheter system. The target and capture device can comprise an elongate member having a distal opening or loop. The target and capture device can comprise a mesh. At least a portion of the target and capture device and/or cerclage traversal catheter system can be imageable.

In another exemplary embodiment, there is featured a kit for repairing a valve in a patient using transcatheter cerclage annuloplasty comprising a cerclage traversal catheter system for introducing a tensioning system through a cerclage trajectory, and target and capture device comprising an expandable and collapsible mesh or a shaft having a proximal end and a distal end with loop at the distal end of the shaft. The mesh can be configured so as to conform to the curvature of the right ventricle when in its expanded state, can have a plurality of openings therein, and can having an imageable target therein. The loop at the distal end of the shaft can be imageable and can be fabricated of a material and configured so as to conform to the curvature of the right ventricle.

Aspects in accordance with this embodiment can include the following features. The target and capture device can be configured so as to provide an imageable target for the cerclage traversal catheter and so as to capture the cerclage traversal catheter system therein. The target and capture device can be provided with a magnet to assist in guiding and capturing the cerclage traversal catheter.

DEFINITIONS

The instant invention is most clearly understood with reference to the following definitions:

"Annuloplasty element" refers to a device that induces reshaping of an annulus of the heart to repair valvular insufficiency. Such devices include those that are placed in the coronary sinus and exert their action by compressive forces on the annulus, for example by expansion of a resilient annuloplasty element, or placement of the annuloplasty element under tension, as in cerclage annuloplasty.

The term "comprises" means "includes without limitation." Thus, "comprising a guiding catheter and a guide wire" means "including a guiding catheter and a guide wire," without excluding additional elements.

The term "subject" or "patient" refers to both human and other animal subjects. In certain embodiments, the subject is a human or other mammal, such as a primate, cat, dog, cow, horse, rodent, sheep, goat, or pig.

As used herein, the terms "suture", "ligature", "tensioning material" and "tensioning element" are often related or interchangeable. For example, as used herein, "suture" is meant to encompass any suitable tensioning element or tensioning device and is not limited to only ligature-based sutures. For example, such tensioning elements can include any suture ligature or device capable of introducing circumferential tension around the mitral annulus to enhance leaflet apposition. It also includes tension-redistribution devices, such as pledgets, and intrinsic variations, such as altered diameter or stiffness. It also includes any form of coronary artery protection devices, particularly in as much as such protection devices are integrated into the tensioning elements/devices. Further, As used herein, the term "ligature" is meant to encompass any suitable tensioning element or tensioning device and is not limited to only suture material. The term "tensioning material" or "ligature" includes sutures and annuloplasty wires. With respect to "tensioning material" or "tensioning element", such terms are defined as any material suitable to perform a coronary sinus mitral valve cerclage annuloplasty, in which circumferential tension is introduced around the mitral valve annulus, such as by placing an encircling material under tension to remodel the mitral valve annulus and enhance leaflet apposition. Examples of suitable tensioning materials are the ligature materials already described.

The term "guide wire" refers to a simple guide wire, a stiffened guide wire, or a steerable guide-wire catheter that is capable of puncturing, traversing, and/or penetrating tissue. The guide-wire also can deliver energy to augment its ability to penetrate tissue, for example by puncturing it, delivering radiofrequency or ultrasound ablative energy or by delivering laser ablative energy. These are examples of a "penetrating device," or "traversal system" (e.g. cerclage transversal catheter system) which is a device capable of penetrating heart tissue, such as the myocardium.

The term "loop" refers to a element that provides an opening capable of capturing and/or ensnaring the cerclage traversal catheter system. Such loops and openings can come in a variety of known geometric shapes which include, but are not limited to, generally circular or elliptical shapes, including cylindrically-shaped ellipsoids and flat ellipsoids, various polygonal shapes, and the like. The loop and/or openings can also be provided in a variety of irregular shapes.

"Mesh" refers to a fenestrated structure formed by two or more strands of wire or other material, or formed by a slotted tube, or formed by interconnected vertebral or disc-like elements interconnected by strands of wire or other material, such that expansion of the mesh expands the fenestrations.

A "mitral valve cerclage annuloplasty" refers to an annuloplasty procedure in which a tensioning element is placed through at least a portion (and preferably all) of the coronary sinus so that the circumferential tension is delivered around the mitral valve annulus and so that a tensioning element can be placed under selective degrees of tension to perform the annuloplasty. An example of cerclage annuloplasty is disclosed in co-pending prior application Ser. No. 11/127,112 (U.S. Patent Publication No. 2005/0216039), and the disclosure of the description of that technique is incorporated herein by reference. However, the mitral valve cerclage annuloplasty technique also includes other cerclage trajectories, such as those disclosed herein, including a trajectory through a proximal coronary septal perforator vein and myocardium or annulus fibrosis interposing between that vein and the right ventricle or right atrium to create circumferential cerclage annuloplasty tension.

All or portions of the devices disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and non-magnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and nickel-cobalt-chromium alloys and Elgiloy, titanium, tungsten, silver, gold, and platinum.

"Shape-memory materials" as used herein, may refer to any known shape memory materials, may include but are not limited to nitinol and elgiloy. They may also include metals that deform to a specified length or shape when exposed to electric current.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "or" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 3A shows an anterior projection view, and FIG. 3B shows a right projection view of the right ventricle and right atrium with the target and capture device in the deployed position.

FIG. 7C in relation to the coronary arteries.

FIGS. 9A-D show an exemplary embodiment of a target and capture device in the form of a mesh made up of a plurality of moveable sinusoidal elements interconnected with horizontal wires, wherein the mesh is in connection with a push member for deployment and manipulation.

DETAILED DESCRIPTION

Figure 1:
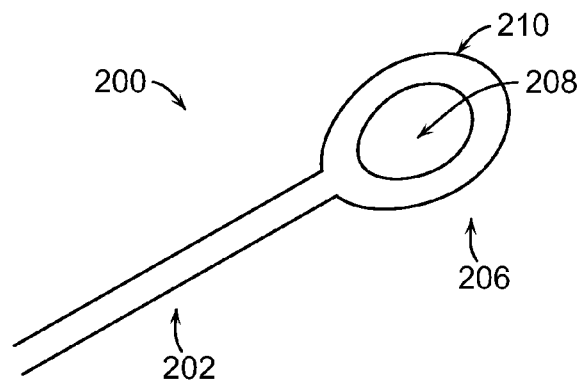
FIG. 1 illustrates the target and capture device in the form of an elongate shaft having a distally located opening accordance with one general embodiment.

The present invention features methods, devices and apparatus for repairing a cardiac valve in a patient. In particular, methods, devices and apparatus are featured for treatment of valvular regurgitation using cerclage annuloplasty techniques. It is noted that while methods, apparatus and devices are described, in particular, in connection with mitral valve repair, such methods, devices and apparatus can also be used in connection with tricuspid valve repair.

The present methods, apparatus and devices can be used in connection with known imaging systems and techniques to image the internal bodily tissues, organs, structures, cavities, and spaces of the subject being treated. For example, the systems and methods described herein can include transmitter or receiver coils to facilitate active-device navigation using an imaging system, such as magnetic-resonance imaging (MRI). This imaging can be conducted along arbitrary or predetermined planes using various imaging methods based on X-ray technologies, X-ray fluoroscopy, MRI, electromagnetic-position navigation, co-registration of X-ray and MRI or of X-ray and CT, video technologies (such as endoscopy, infra-red imaging, saline-flush videoscopy and the like), ultrasound, and other such technologies. In some embodiments, real-time MRI (rtMRI), intracardiac ultrasound, or electromagnetic guidance is employed. Thus, as used herein, the term "imaging system" includes any device, apparatus, system, or method of imaging the internal regions of a subject's body.

Methods of the invention generally include introducing a tensioning material around the cardiac valve annulus via a cerclage trajectory with the assistance of a target and capture device, and placing the tensioning material under tension. A cerclage traversal catheter system, is inserted into the vasculature of a patient and is guided through a cerclage trajectory, while the target and capture device is also introduced into the vasculature of the patient and positioned within the cerclage trajectory, particularly at a "reentry site" at the end of the desired cerclage trajectory. Any suitable cerclage trajectory can be used, such as those previously disclosed, for example, in U.S. Published Patent Application Nos. 2005/0216039 and 2010/0049314. The cerclage traversal catheter system can traverse the cerclage trajectory (e.g. under imaging guidance), and further with the assistance of the target and capture device. In particular, the cerclage traversal catheter system, with the assistance of the target and capture device, reenters the right ventricle or right atrium through the desired reentry site where it is further ensnared or captured by the target and capture device. The cerclage traversal catheter system is then retrieved and replaced with the tensioning material. Any known tensioning materials can be used such as a suture, particularly a cerclage suture. Tension can then be applied to the tensioning material to a desired degree, such as under imaging guidance, and thereafter fixed using a tension fixation device.

In addition to the cerclage traversal catheter system, which is introduced to apply the circumferential tensioning element, a target and capture device is further introduced which works together with the cerclage traversal catheter system so as to guide the cerclage traversal catheter system through the desired trajectory. In particular, the target and capture device is positioned in the trajectory at a desired site, and the cerclage traversal catheter system must be guided or passed through the target and capture device so as to precisely follow the trajectory. For example, the target and capture device can be provided at a particularly difficult point in the trajectory so as to facilitate proper guidance of the cerclage traversal catheter system through such difficult points. In certain embodiments, the target and capture device is positioned at a desired "reentry site" of a cerclage trajectory that includes, for example, the coronary sinus, great cardiac vein, basal septal perforator vein, followed by traversing a segment of the interventricular myocardial septum to reenter the right ventricle or right atrium ("reentry site"). In such a trajectory, the reentry site can be particularly difficult to traverse and, as such, the target and capture device provides a target for guiding the cerclage traversal catheter system through the desired reentry site. In certain embodiments, the target and capture device is configured, arranged and/or positioned so as to serve as an imaging target for the steerable cerclage traversal catheter system as it passes through a desired reentry site (e.g. from the coronary venous system through the heart to emerge into the right heart chamber).

In certain embodiments, the target and capture device is configured, arranged and/or positioned so as to displace desired structures so as to prevent entrapment and/or injury to such structures as the cerclage traversal catheter system traverses the cerclage trajectory or after the cerclage tensioning element is shortened to apply annuloplasty tension. For example, the target and capture device is configured, arranged and/or positioned so as to displace the right ventricular trabecular and tricuspid subvalvular structures (trabeculae carnae, chordae tendinae, moderator band) away from the right heart cavity against the right ventricular endocardial surface. As such, the cerclage traversal catheter system can be prevented from entrapping or injuring these structures once it is recaptured and replaced with a tensioning element or related device.

The target and capture device can, further, advantageously be configured so as to conform to the curvature of the right ventricle by having inner and outer curvature longitudinal elements of different lengths that impart curvature. The device, in particular, conform to the three-dimensional dextro-curve configuration of the anatomic right ventricle by virtue of having shape-memory imparted into them.

The target and capture device can, further, advantageously be configured so as to as capture and/or ensnare the cerclage traversal catheter system as or after the cerclage traversal catheter system passes through the desired reentry site. As such, trabecular entrapment can be avoided. The target and capture device, as such, can be provided in any configuration that will provide a target to the cerclage traversal catheter system as it traverses a cerclage trajectory, and such that the target and capture device will capture or ensnare the cerclage traversal catheter system as/or after the cerclage traversal catheter system passes through the target. In certain embodiments, the target and capture device is configured, arranged and/or positioned so as to capture or ensnare the cerclage traversal catheter system as it enters the right heart, without capturing or entrapping cardiac structures. In certain embodiments, the target and capture device is further configured, arranged and/or positioned so as to retrieve the captured cerclage traversal catheter system.

The target and capture device can further be configured and arranged such that it provides counter-pressure for the application of traversal force. In particular, the target and capture device can be configured and arranged so as to apply pressure to or push against a target area such as the myocardium septum. Such application of pressure against the myocardium septum facilitates crossing of the myocardium septum with the cerclage transversal catheter system. For example, the target and capture device can be provided with sufficient rigidity and in any desired shape so as to allow for application of pressure at a target area.

Figure 2:
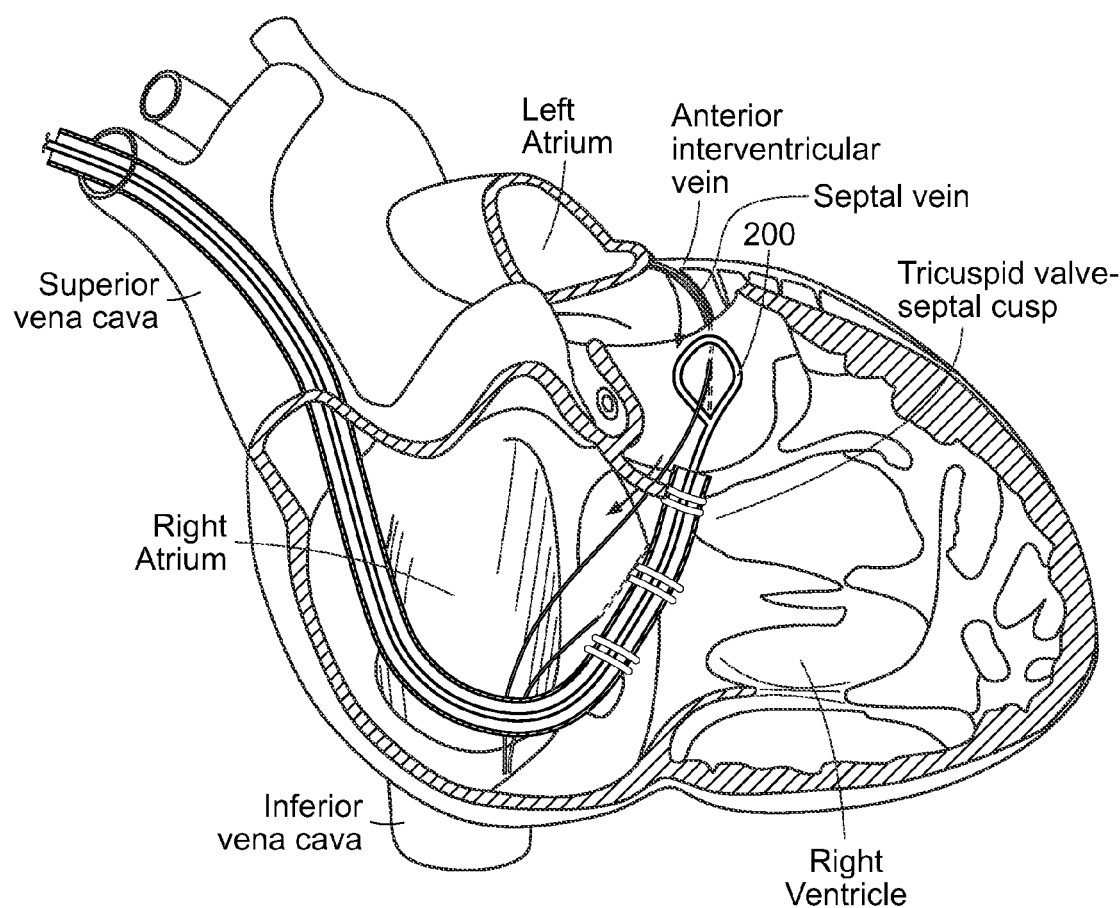
FIG. 2 shows the target and capture device in of FIG. 1 as positioned at a cerclage reentry site via a guiding catheter.

An embodiment of a target and capture device 200, is shown in FIG. 1. The device 200 generally comprises an elongate body or shaft 202 having a proximal end (not shown), a distal end 206, and an opening 208 at or near the distal end 206. As shown, a loop 210 having an opening 208 can be provided at the distal end 206. A target and capture device 200 having an elongate body or shaft 202, a proximal end (not shown), a distal end 206 and a loop 210 is further shown in FIG. 2 positioned at a desired cerclage trajectory target site via a guiding catheter. In accordance with this embodiment, the opening 208 provides a bullseye-like target and snare mechanism for the cerclage traversal catheter system. The loop 210 and/or opening 208, for example, is shown as being enlarged and positioned based on the shape and design of the device so as to provide a suitable target and snare mechanism. As shown in FIG. 1, a single loop 210 having a single opening 208 is provided at the distal end 206 of the shaft 202. However, it is noted that a plurality of loops and openings could also be provided. Further, while the loop and opening are depicted as generally circular in shape, the loop and/or opening can be provided in any shape as long as it is capable of providing a target for the cerclage traversal catheter system as it passes through the cerclage trajectory and provided it is capable of capturing or ensnaring the cerclage traversal catheter system. For example, cylindrical rectanguloid, cylindrically-shaped ellipsoid, or flat ellipsoid type configurations can be provided.

The target and capture 200 device can be made of any suitable material or combination of materials that provide both the strength and flexibility suitable to resist collapse by external forces, such as forces imposed during bending or twisting as the target and capture device 200 is introduced to the cerclage trajectory site, and which allows the target and capture device 200 to be properly positioned and torqued at the desired cerclage site as described herein. In certain embodiments, the device 200 is made of a metal such as nitinol or steel, or a polymer, or a combination of metal and polymeric materials. Insulation gaps can be provided in the target and capture device to allow an array of electrodes to localize points of contact, multiplexed through strands. In certain embodiments, the target and capture device 200 is fabricated of a shape memory material wherein the loop 210 has a specific right-ventricular conforming "remembered" shape, and a collapsed shape for delivery before positioning to the target site and for withdrawal from the target site. In certain embodiments, at least a portion of the target and capture device, such as the loop 210, is formed of a shape memory material such that the loop has a remembered shape that conforms to the curvature of the right ventricle. As such, upon deployment of the target and capture device to the cerclage reentry site in the right ventricle, the loop can take on the remembered shape for properly positioning.

In certain embodiments, the specific shape of the device is custom-fabricated for individual patients based on two- and three-dimensional imaging-based models to determine the dimensions and geometry of the right ventricle and the cerclage reentry site. These models may also be used to select an optimal target. These models may be based upon tomographic, 3-dimensional, or 2-dimensional X-ray fluoroscopy, computed tomography, ultrasound, magnetic resonance imaging, or electroanatomic positioning-based maps.

In certain embodiments, the target and capture device 200 is provided with a loop 210 that is adjustable (e.g. in size) such that after the cerclage traversal catheter system has passed therethrough, the loop 210 is adjusted so as to capture or ensnare the cerclage traversal catheter system therein. In some embodiments, the loop 210 is formed of a shape memory material wherein the loop can alternate between a target configuration, wherein the loop is provided in an open state at the cerclage trajectory target site, and a capture or ensnare configuration, wherein the loop collapses about the cerclage traversal catheter system so as to capture or ensnare it.

As such, the loop 210 can be formed such that the nominal (i.e. collapsed or ensnaring) diameter is slightly less than the diameter of a distal portion of the cerclage traversal system (e.g. for a 0.014" traversal system, the nominal slot width could be 0.009-0.013" in diameter). Based on the size of the cerclage traversal catheter system which can of course vary, the proper nominal size of the loop could likewise be appropriately selected.

In certain embodiments, at least a portion of the target and capture device 200 is imageable. Any known imaging systems and techniques to image medical devices and/or the internal bodily tissues, organs, structures, cavities, and spaces of the subject being treated can be used. In some embodiments, a receiver coil can be incorporated to determine the position of the target and capture device 200 in relation to local electromagnetic field registered with anatomic images. In some embodiments, at least the portion of the device surrounding the opening 208, or at least a portion of the loop 210 is imageable. As such, the opening 208 or loop 210 can be properly positioned at the desired site of the cerclage trajectory with the assistance of imaging techniques, and the opening 208 or loop 210 can provide an imageable target to and/or through which the cerclage traversal catheter system can be properly directed. The target and capture device can, in some embodiments, be positioned according to right ventricular anatomy, geometry, and even electrophysiological function using selected imaging guidance (e.g. EP intracardiac electrode elements can be integrated into shaft 202) Such imaging techniques and materials are well known and could also suitably be used in connection with the target and capture device 200. In certain embodiments, asymmetric radiopacity is provided in different portions of the target and capture device 200 so as to, for example, indicate anterior and posterior elements in different x-ray projection angles.

As provided in some embodiments, the target and capture device 200 is further configured to conform to the curvature of the right ventricle, which is the "reentry site" in certain desired cerclage trajectories. For example, the target and capture device 200 can comprise a loop 210 configured to conform to the unique curvature of the right ventricle. As such, the loop 210 can be geometrically shaped to model or conform to the inflow-septal-infundibular curvature of the right ventricular septum and outflow tract, and designed to assure apposition to the septal wall and to allow recapture of the cerclage traversal catheter system as it reenters the heart from the great cardiac vein across the interventricular septum. The snare loop can be made of nitinol wire or other metal wires with similar features and, using the superleasticity and shape memory properties of the snare loop, it can be shaped to conform the desired right ventricule curvature. In particular, the shape of the loop can be modeled on the typical septal infundibular right ventricular anatomy, which resembles an ellipsoid that conforms to a cylinder that is then twisted. The loop 210, being configured so as to conform to the curvature of the right ventricle, can be torqued to abut the right ventricular septum in the desired reentry site so as to enhance procedural targeting and cerclage traversal catheter system retrieval which, further, can reduce the likelihood of trabecular entrapment. A torque-fixation device or mechanism can further be provided so as to maintain constant apposition of the target and capture device 200 with the right ventricle. For example, any single or coaxial catheter pair can be used to impart torque, and a hemostatic valve or the like can be used to fix the torque against an introducer sheath. In some embodiments, the delivery catheter is provided with one or more lumen that can be configured to determine anatomic position relative to the tricuspid valve and pulmonic valve, e.g. based on phasic blood pressure signatures of the right atrium, right ventricle and pulmonary artery.

The target and capture device 200 can be introduced to the site through a suitable delivery catheter, and, in some embodiments, can be introduced through the same delivery catheter that is used to introduce the cerclage traversal catheter system. In certain embodiments, the target and capture device 200 is introduced via a delivery catheter from a cephalad (typically transjugular or from upper extremity veins) or caudad (typically transfemoral) approach. In an exemplary embodiment, the target and capture device 200 allows for removal from the same sheath as the cerclage traversal catheter system, which further allows both free ends of the cerclage traversal catheter system to be externalized through the same orifice (i.e. the target and capture device 200 ensnares and externalizes the cerclage traversal catheter system through the same sheath that the cerclage traversal catheter system was introduced through). In some embodiments, the delivery catheter is provided with an outer diameter of 4 Fr to 8 Fr, and is provided with a lumen having a distal or side-exit opening for targeted deployment of the target and capture device 200. To provide enhanced positioning of the target and capture device 200 at the desired cerclage trajectory site (e.g. reentry site), the delivery catheter can be provided with a lumen capable of delivering, positioning, torquing, and apposing the target and capture device 200 at the desired site. In certain embodiments, the target and capture device 200 is provided with a loop 210 that conforms to the dorsomedial "right handed" curvature of the right ventricle, and appropriate counterclockwise torque of the target and capture device 200 alone or together with the delivery catheter maintain apposition of the loop 210 with the right ventricular septum along the expected cerclage reentry site. In some embodiments, an over-the-wire lumen can be provided in the target and capture device 200 to position along the right ventricular outflow tract. In certain embodiments, markers can be provided in the target and capture device 200 and/or the delivery catheter so as to provide the user with the ability to determine the insertion length and/or the rotational position of the target and capture device 200 relative to the delivery catheter.

Another embodiment of a target and capture device 300, is shown in FIGS. 3A-4B. The target and capture device 300 generally comprises a mesh, preferably an expandable and collapsible mesh 302. The mesh 302 is configured for deployment at a desired cerclage trajectory site so as to guide and simplify capturing the cerclage traversal catheter system as it traverses the cerclage trajectory.

In some embodiments, the mesh 302 is configured so as to provide a target for the cerclage traversal catheter system as it reenters the right ventricle or right atrium to ensure that the cerclage traversal catheter system reenters at the proper cerclage trajectory. In certain embodiments, the target is a center portion 304 of the mesh 302 (for example, as depicted by the shaded portion of the mesh 302 in FIG. 4A), or any other portion of the mesh in any size or shape. In other embodiments, the target is an opening 306 in the mesh 302 (for example, as shown in FIG. 4B wherein a centrally located opening is provided as the target). For example, the mesh 302 can be provided in the form of a plurality criss-crossing wire-like members 304 which form a plurality of openings, for example, as shown in FIGS. 3A-4B. The target, thus, could be any of the openings positioned at the desired cerclage target site. The target may also be based upon patient-specific two- and three-dimensional imaging-based models to determine the dimensions and geometry of the right ventricle and the cerclage reentry site. These models may be based upon tomographic, 3-dimensional, or 2-dimensional X-ray fluoroscopy, computed tomography, ultrasound, magnetic resonance imaging, or electroanatomic positioning-based maps.

In certain embodiments, at least a portion of the mesh can be imageable so as to facilitate proper positioning of the mesh at the desired reentry site under imaging techniques, and such that the cerclage traversal catheter system can be guided into and/or through the target reentry site via the mesh under imaging techniques. For example, unique radiopaque markers can be incorporated to allow targeted positioning of the mesh 302 and guidance of the cerclage traversal catheter system in relation to electrograms or anatomy or the position of the coronary sinus. In some embodiments, a receiver coil can be incorporated to determine the position of the mesh 302 in relation to local electromagnetic field registered with anatomic images. In some embodiments, a portion or "cell" of the mesh 302 is provided with an imageable target marked thereon which can positioned, under imaging, at the desired cerclage trajectory location so that the cerclage traversal catheter system can be guided to the target. In some embodiments, one or more openings (not shown) in the mesh 302 are imageable and are provided as a target for the cerclage traversal catheter system (e.g. target 304 or opening 306) and, as such, can be properly positioned at the desired cerclage trajectory location so that the cerclage traversal catheter system can be guided to the properly positioned opening. In certain embodiments, asymmetric radiopacity is provided in different portions of the mesh 300 so as to, for example, indicate anterior and posterior elements in different x-ray projection angles. Any known imaging techniques could suitably be used.

In certain embodiments, the mesh 302 is configured so as to be capable of capturing and/or ensnaring the cerclage traversal catheter system during a cerclage procedure. In certain embodiments, an expandable or collapsible mesh 302 is configured such that, when expanded or deployed (for example, as shown in FIGS. 3A-4B), the mesh 302 can be positioned at the desired cerclage trajectory target site, and such that when or after the cerclage traversal catheter system contacts the mesh, the mesh is collapsed 302 about the cerclage traversal catheter system thereby capturing and/or ensnaring it.

For example, in an exemplary embodiment, the mesh 302 is formed of two or more wire elements that separate when deployed and adjoin when retracted, such that the cerclage traversal catheter system becomes snared or captured in the adjoined wire elements. In certain embodiments, the expandable and collapsible mesh 302 is provided with openings in the mesh 302, and the mesh 302 is configured such that when the mesh 302 is collapsed, the cerclage traversal catheter system becomes captured or ensnared within a target opening.

Figure 5A:
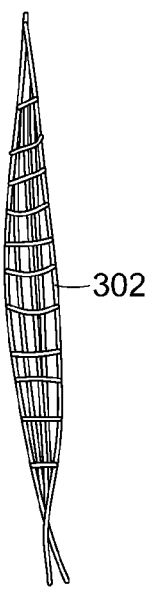
FIGS. 5A and 5B illustrate a target and capture device in the form of an expandable (FIG. 5B) and collapsible (FIG. 5A) mesh.
Figure 5B:
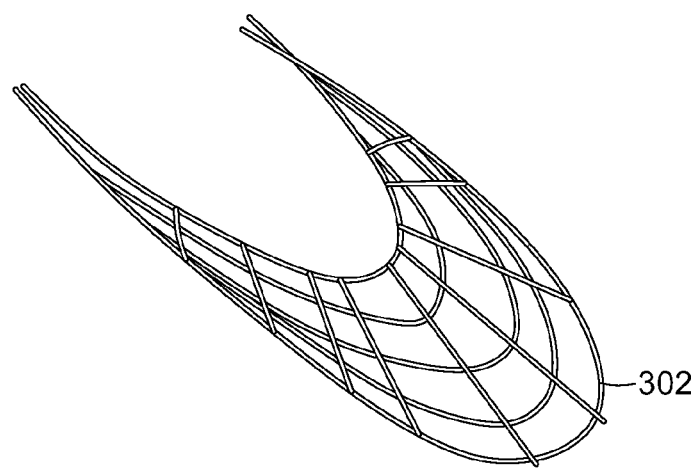

In yet further embodiments, the mesh 302 is configured so as to conform to the desired cerclage target site. For example, the mesh can be shaped to appose the right ventricle and right ventricular outflow tract from either a transjugular or transfemoral approach. In an exemplary embodiment, the mesh 302 is provided in a collapsed state (for example, as shown in FIG. 5A) that facilitates insertion and delivery through a suitable delivery catheter, and the mesh 302 is further provided with an expanded state (for example, as shown in FIG. 5B) that conforms to the curvature of the right ventricle.

In certain embodiments the mesh 302 is disposed at a reentry site in the right ventricle and is configured so as to exert pressure against trabecular-papillary elements of the tricuspid. In particular, the mesh 302 can be configured to apply pressure so as to displace the valvar chordae and the true and false trabecular muscles temporarily against the endocardial border of the right ventricle during right ventricular reentry of a cerclage traversal catheter system crossing the interventricular septum between the coronary venous system and the right ventricular cavity.

The mesh 302 can apply this pressure by virtue of cerclage traversal catheter system. By abutting the right ventricular reentry site of the cerclage traversal catheter system, the reentering cerclage traversal catheter system is forced to cross the mesh, and trabecular entrapment can beneficially be avoided. In particular, during septal-perforator to right-ventricular myocardial traversal, the mesh 302 can be positioned so as to appose the mural tricuspid subvalvular apparatus to the septal myocardial wall which, thereby, forces the reentering cerclage traversal catheter system to cross only the nearest orthogonal trabecular "window" as it passes from the ventricular septum to the right ventricular cavity. Further, the mesh 302 is designed and disposed so as to allow ensnarement of the reentering cerclage traversal catheter system. As a result, trabecular entrapment is avoided.

Figure 3A:
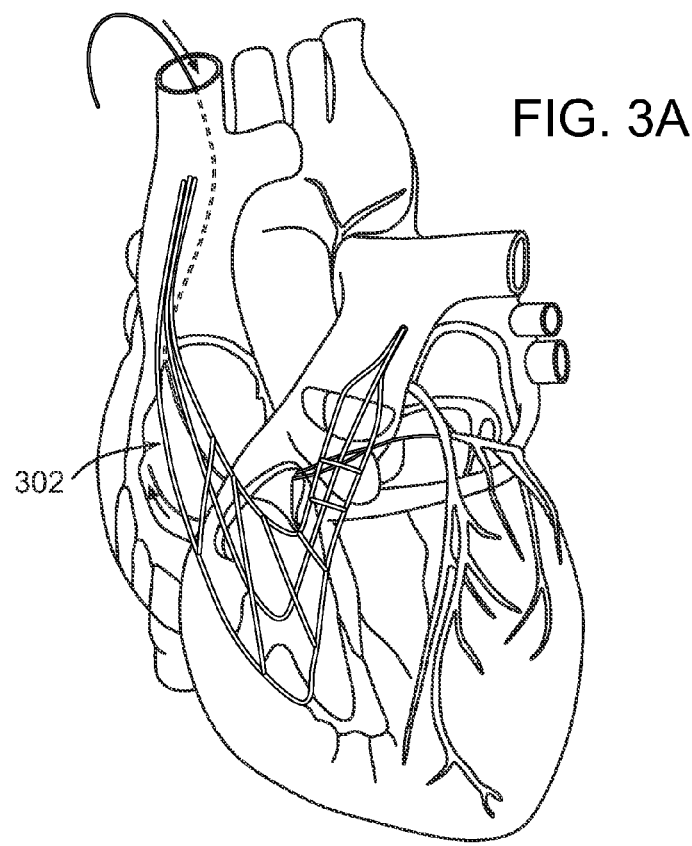
FIGS. 3A and 3B illustrates a target and capture device in the form of a mesh in accordance with a second embodiment of the present invention as positioned during a percutaneous cerclage annuloplasty procedure. Particularly.
Figure 3B:
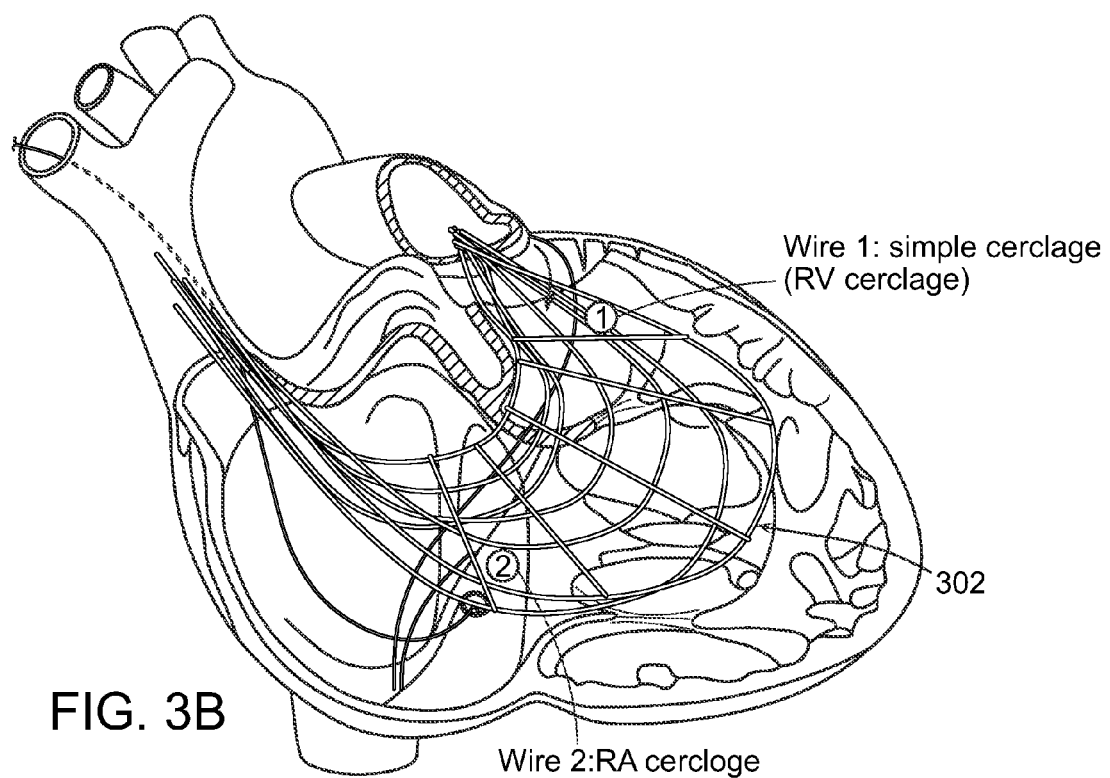
Figure 4A:
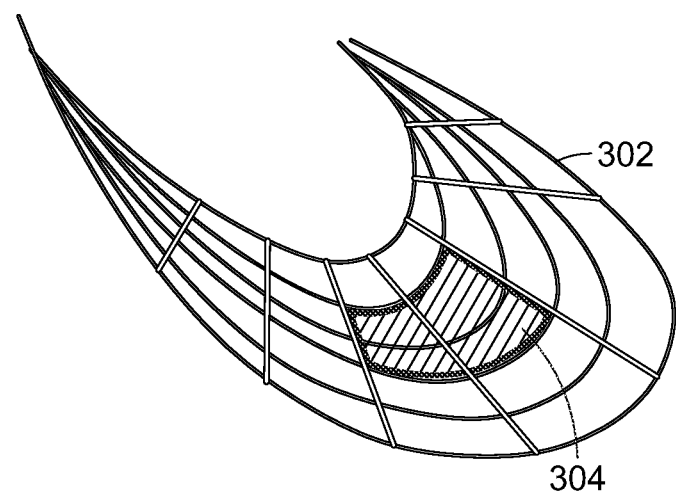
FIGS. 4A and 4B illustrate various possible a target sites in a and capture device in the form of a mesh.
Figure 4B:
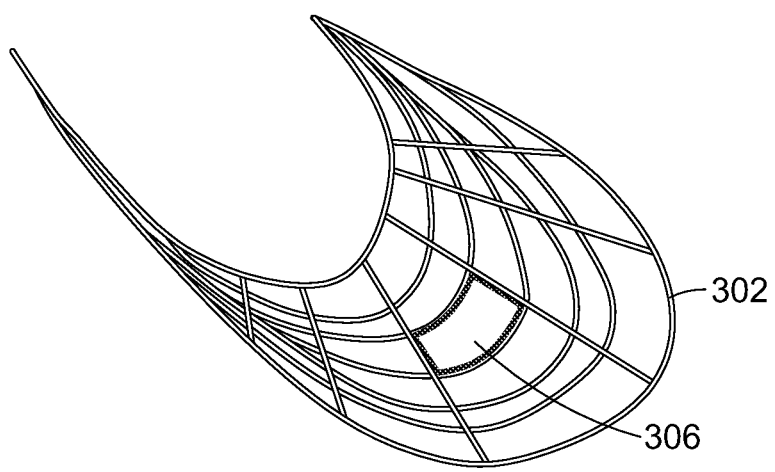
Figure 6:
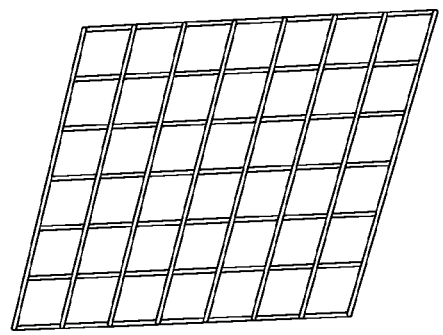
FIG. 6 illustrates a target and capture device in the form of a flat mesh.

In some embodiments, the expanded mesh 302 forms a basket-like U-shape (e.g. see FIGS. 3A-B that conforms with the geometry of the right ventricular inflow and outflow tract along the interventricular septum. In yet other embodiments, a flat mesh design (e.g. see FIG. 6) can be provided so as to conform with the septum along the right ventricular inflow and outflow and can utilize torque (e.g. counterclockwise from the neck) to appose against the septum. In certain embodiments, the mesh 302 in its collapsed form is introduced to the cerclage reentry cite from a cephalad (typically transjugular or transaxillary) or caudad (typically transfemoral) approach. The collapsed mesh 302 can, further, be removed from the same delivery catheter as the cerclage traversal catheter system such that both free ends of the cerclage traversal catheter system can be externalized through the same sheath (i.e. the target and capture device in the form of a mesh 300 ensnares and externalizes the cerclage traversal catheter system through the same sheath that the cerclage traversal catheter system was introduced through). In any of these embodiments, the mesh 300 can be fabricated of a shape memory material so that the mesh 300 can alternate between a collapsed shape and an expended shape. In some embodiments, the expanded shape is a shape that conforms to the target cerclage location, such as the reentry site. In other embodiments, the expanded shape provides the mesh in a form suitable for providing a target for the cerclage traversal catheter system, while the collapsed shape provides the mesh in a form suitable to capture or ensnare the cerclage traversal catheter system and for removal of the mesh.

Proper positioning of the target and capture device can generally be facilitated based on the device's unique shape conformance to the inner and septal curvature of the right ventricle, based on imaging guidance, and/or based on local intracardiac electrogram signal and timing such as the atria, atrioventricular node, Bundle of His, bundle branches, and right ventricular depolarization. In some embodiments, the catheter used to deliver the mesh target and capture device 302 is provided with one or more lumen that can be configured to determine anatomic position relative to the tricuspid valve and pulmonic valve, e.g. based on phasic blood pressure signatures of the right atrium, right ventricle and pulmonary artery. Further, angiographic lumen can be provided so as to allow angiography to conform the position of the mesh against the right ventricle. Still further, one or more unipolar or bipolar electrodes can be provided to acquire intracardiac electrograms so as to aid in positioning (e.g. by determining the position of the delivery catheter and/or the mesh 302 in relation to continuous myocardial depolarization and repolarization patterns, including HIS electrograms, near- and far-field atrial and ventricular electrograms). Still further, one or more electrodes can be provided to contact intracardiac electrograms to detect contact of the delivery catheter and/or mesh 302 with cardiac structures such as the moderator band and ventricular septum. In further embodiments, a catheter or wire can further be used with the delivery catheter and/or mesh 302 to engage the coronary sinus and properly set out the cerclage trajectory.

In some embodiments, the mesh 302 is connected to a delivery mechanism, such as a shaft/push member or the like, for deployment and retrieval from the target cerclage site. For example, as shown generally in FIG. 9, the mesh 302 can be deployed through a delivery sheath 410 via a push member 412 to the desired site. As shown in FIG. 9A, the mesh 302 is in connection with a push member 412 which is used to deploy the mesh 302 from the delivery sheath 410 into the right ventricle. In certain embodiments, the mesh 302 expands as described herein to apply pressure against the target site.

In an exemplary embodiment, for example as shown in FIGS. 9A-D, the mesh 302 is deployed through a delivery sheath 410 via a push member 412 to the desired site where it fills the right ventricular space to displace trabecular structures and avoid their entrapment after recovery of the cerclage traversal catheter system. In certain embodiments, the mesh is composed of a preshaped memory-metal frame that expands to the desired shape on deployment. As shown in FIGS. 9A-D, the mesh 302 can be in the form of a plurality of sinusoidal structural components or rings 414 interconnected with wires 416 or the like extending along the length of the mesh 302 so as to form openings 418 in the mesh 302. The sinusoidal or ring components 414 can move freely over the wires 416 (as depicted by the arrows in FIG. 9C) and can further be connected to each other with wires 422, which are preferably expandable and collapsible (e.g. as depicted in the Figures, the wires 422 are provided in one embodiment with an accordion-like or similar shape). Movement of the sinusoidal rings 414 can be controlled by push member 412. As such, the mesh 302 could be used as follows: first the whole mesh structure 302 is deployed in the right ventricle; the cerclage traversal catheter system is then used to reenter the right ventricle at the targeted location; next the sinusoidal rings 414 are pushed toward the distal end while retaining the cerclage traversal catheter system tip 425 inside the deployed mesh structure 302; the sinusoidal ring 414 positions are then locked in place while the mesh 302 is pulled inside the delivery sheath 412 via the push member 412 to capture and retrieve and externalize the ensnared cerclage traversal catheter system 420.

Figure 12A:
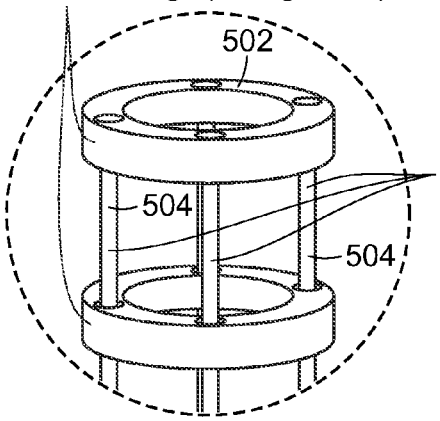
FIG. 12 shows a further embodiment of a target and capture device in the form of a vertebrated skeleton catheter comprising interconnected disks.
Figure 12:
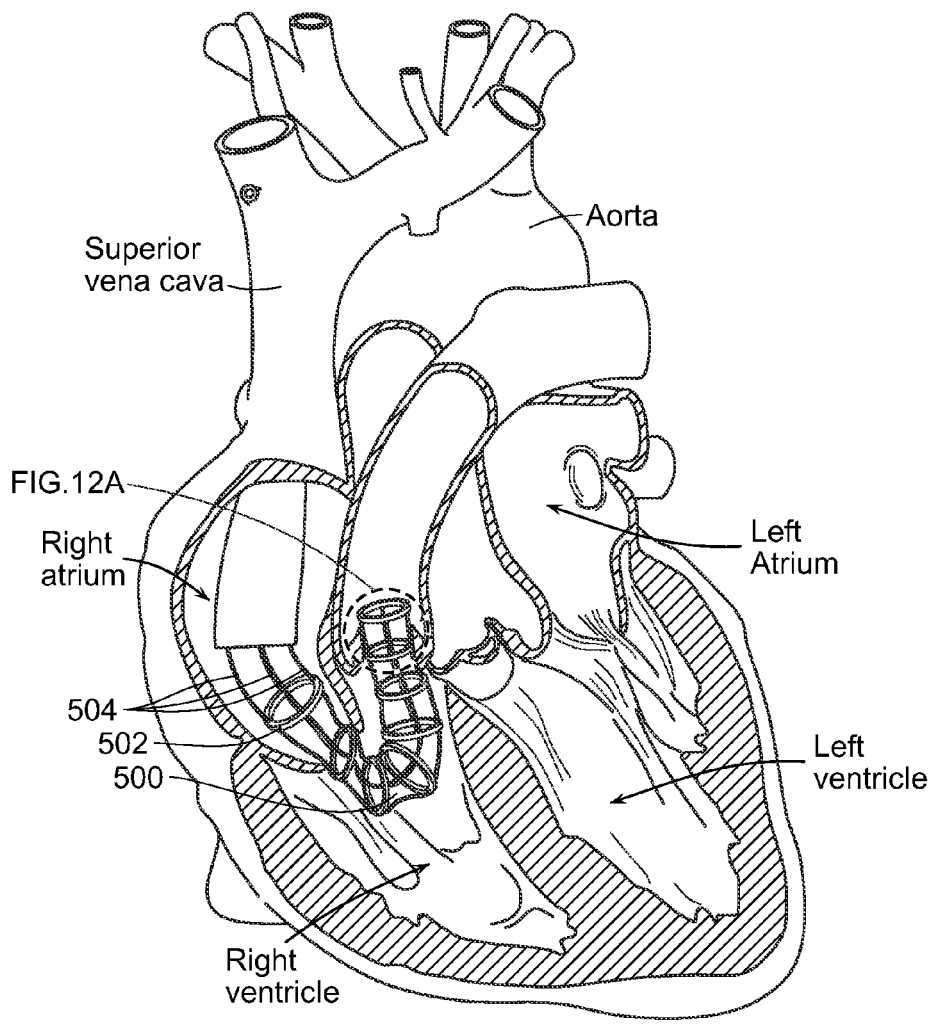

Another embodiment of a target and capture device in the form of a "mesh" is shown in FIG. 12. In particular, the mesh is in the form of a vertebrated skeleton catheter 500 generally comprising a plurality of vertebral elements, such as hollow centered disc-like elements 502, interconnected through a plurality of wires 504 or the like for tensioning of the elements 502. It is noted that while a disc-like shape is depicted, any other geometry could likewise be adapted. Openings (which can be configured and used similarly to the openings in the above-described mesh configurations) are formed between the elements 502 and wires 504. Tension can be independently provided to individual wires 504 so as to adjust the shape of the vertebrated skeleton catheter 500 by, for example, adjusting the distance between adjacent disks 502 and/or angling the disks 502 with respect to each other such that the vertebrated skeleton catheter 500 assumes the specified right-handed curve of a target right ventricle inflow-to-outflow tract. As such, the vertebrated skeleton catheter 500 can beneficially apply pressure at the site and displace anatomical structures as desired and described herein. The vertebrated skeleton catheter 500 can further be configured and arranged so as to capture, ensnare and/or externalize the cerclage traversal catheter system between adjacent disks 502 and/or wires.

In yet another embodiment, a "mesh" target and capture device is in the form of an expanding slotted tube, which can, for example, be in the general form of a tube having cuts or slots along at least a portion of its length. The expanding slotted tube can be suspended or supported on proximal and distal ends, such that when the proximal and distal ends are drawn toward each other (for example, by a deployment catheter), the expanding slotted tube assumes the right-handed shape of the right ventricle inflow-to-outflow tract geometry. The expanding slotted tube can be fabricated of any of the materials described herein in connection with the target and capture device, and in some embodiments is formed of a shape-memory material. In some embodiments, the expanding slotted tube is fabricated of Flexinol such that current can be applied or not applied so as to alternate between desired configurations. As such, the expanding slotted tube can beneficially apply pressure at the deployed site and can further displace anatomical structures as desired. The cells (i.e. openings) of the slotted metal tube can further be configured and positioned so as to capture and entrap the cerclage traversal catheter system for retrieval and externalization. In particular, when the expanding slotted tube is compressed, with the openings pressed together or tightened, the openings grip and entrap the cerclage traversal system.

In any of these mesh configurations, the openings in the mesh can have a nominal (compressed or entrapping) diameter slightly less than the diameter of a distal portion of the cerclage traversal system (e.g. for a 0.014" traversal system, the nominal slot width could be 0.009-0.013" in diameter). Based on the size of the cerclage traversal catheter system which can of course vary, the proper nominal size of the openings could likewise be appropriately selected.

As described above, in some embodiments a target and capture device in the form of a loop 202, mesh 310, vertebrated skeleton catheter 500 or slotted-metal tube can be used alone to provide all or any combination of one or more of the following features as further described herein: provide a target for the cerclage traversal catheter system at a desired reentry site, apply pressure at a target site, capture the cerclage traversal catheter system, ensnare the cerclage traversal catheter system, and externalize the cerclage traversal catheter system.

Figure 11:
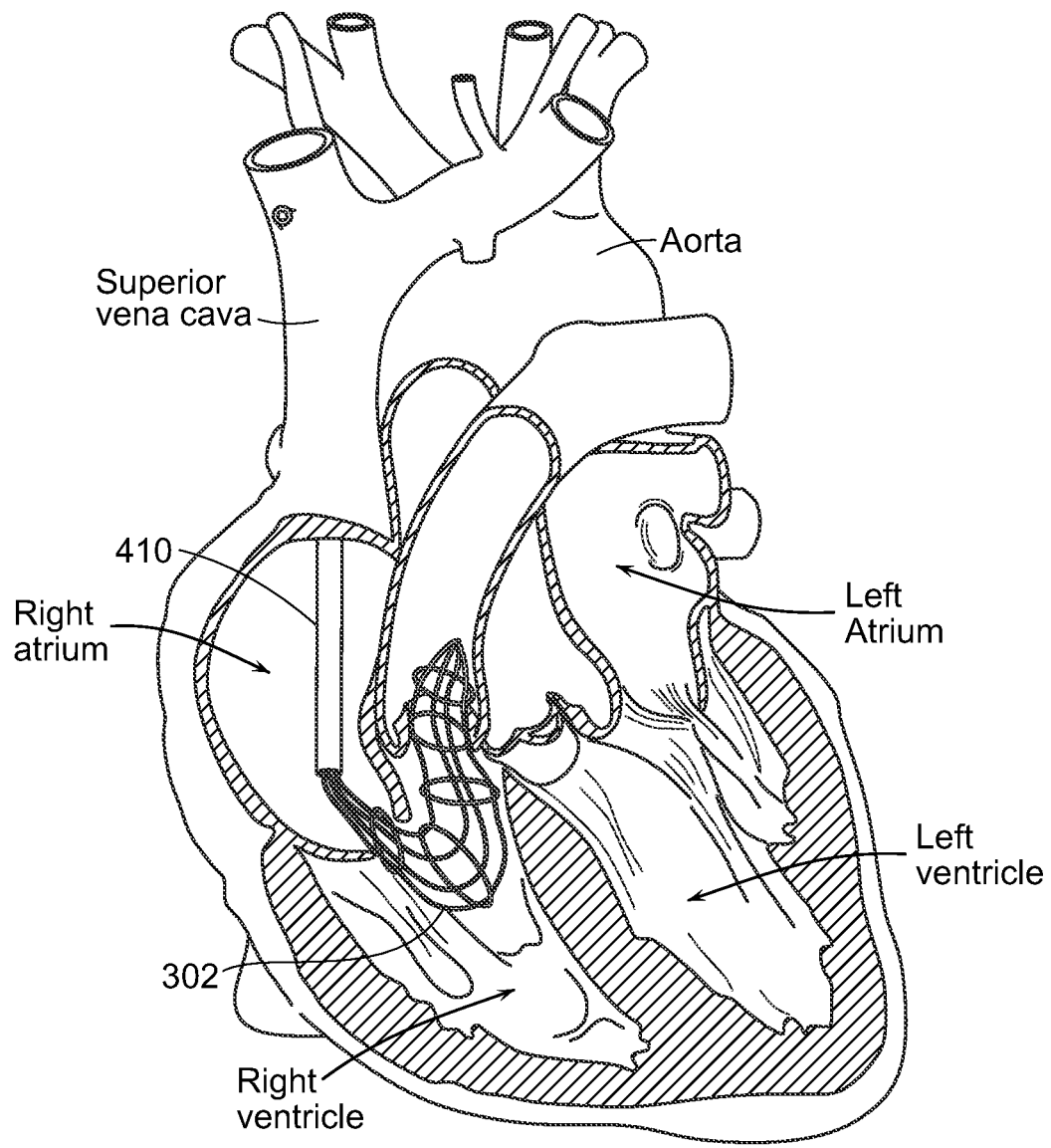
FIG. 11 shows an embodiment of a mesh target and capture device deployed to conform to the right ventricular geometry.

In some embodiments, two or more devices, such as one or more loop devices 210, one or more mesh 302, one or more vertebrated skeleton catheters 500, and/or one or more slotted-metal tubes can be used in combination to provide the all or any combination of the above-described features. For example, a mesh 302 can be used together with a capture or snare device, such as the loop 210, as described herein. As such, the mesh 302, which serves as a displacement device, can be deployed and positioned at the target site so as to apply pressure and displace trabecular structures to avoid trabecular entrapment, for example as depicted in FIG. 11. A separate capture or snare device, for example, a pre-shaped snare or loop 210 is deployed and positioned at the target reentry site so as to provide the cerclage traversal catheter system with a target site through which it is to pass, and so as to capture the cerclage traversal catheter system. A pre-shaped snare can be beneficially provided and configured so as to assure that when the cerclage traversal catheter system reenters the right ventricle it is forced to remain inside the snare loop. The shape of the loop is preferably modeled on the typical septal infundibular right ventricular anatomy, which resembles an ellipsoid that conforms to a cylinder that is then twisted. In certain embodiments, a pre-shaped snare recovery device is further provided and is advanced over the pre-shaped snare device to reduce the diameter of the snare loop and capture the cerclage traversal catheter system, preferably while not changing the orientation of the snare loop.

Figure 10:
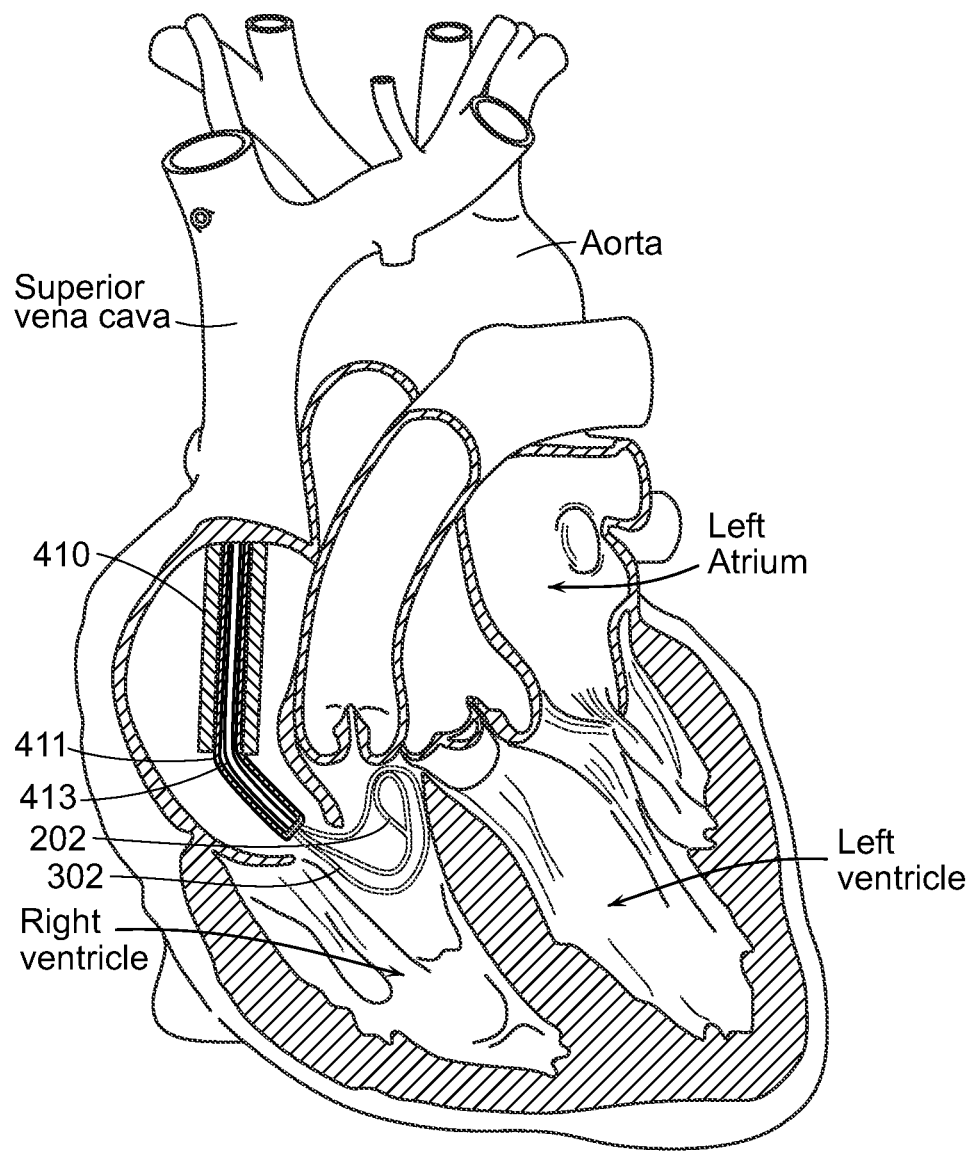
FIG. 10 shows an embodiment wherein a mesh is used in combination with a snare loop.

FIG. 10 shows an example of a dual device system in use. As shown, at least three coaxial catheters 410, 411, 413 are positioned in the right ventricle from the inflow to outflow tract. The outer catheter 410 delivers the deployable mesh 320, which is deployed to conform to the right ventricular geometry (e.g. as depicted in more detail in FIG. 11), which displaces trabeculations to avoid inadvertent trabecular entrapment of the reentering cerclage traversal system, and which can also allow for ensnaring and retrieval of the reentering cerclage traversal system. A central coaxial catheter 413 can form the push mechanism which deploys the mesh 302 and which can be used to modify the shape of the mesh 302 (e.g. by moving sinusoidal elements 414 as described in connection with FIGS. 9A-D), and which can further be used to position a snare/loop 202 at the target reentry site to capture the reentering cerclage traversal system.

An exemplary method, which uses the devices and apparatus described herein, is described below. In particular, the methods describes a percutaneous-transmyocardial-cerclage annuloplasty using tension sutures and a target and capture device. This embodiment is directed at (but not limited to) treating Carpentier-Type-I mitral-valve regurgitation, in which valvular regurgitation is related to annular dilation associated with underlying cardiomyopathy. In the Carpentier-Type-I condition, valve-leaflet mobility and alignment are normal, but the leaflets do not sufficiently appose one another to prevent regurgitation of blood into the left atrium. This lack of valvular apposition can result from a variety of diseases or physiological defects, such as myocardial-annular dilation following a myocardial infarction or non-ischemic cardiomyopathy. While this description relates to the mitral valve, this procedure can be readily adapted to other cardiac valves, such as the tricuspid valve, or other similar tissues and structures of a subject's body.

Briefly, a guiding catheter (GC) is inserted percutaneously into the vasculature of a subject, such as into the femoral vein, and guided through the vasculature into the heart. Access to the mitral valve can be accomplished in a variety of ways. Additionally, a non-percutaneous approach can be employed, if necessary or desired. Once the distal end of the GC is in place, the cerclage traversal catheter system is introduced into the lumen of the GC and traversed through the GC. A target and capture device in the form of a loop/snare or any of the mesh configurations, e.g. 200/300/500, is further introduced into the vasculature of a patient via a delivery catheter that can be a separate delivery catheter or can be the same GC used to introduce the cerclage traversal catheter system. The target and capture device 200/300/500 is then positioned at a desired target site in the cerclage trajectory, such as a "reentry site" as described herein (e.g. see FIGS. 2 and 3A-B).

According to one exemplary embodiment, the distal end of the cerclage traversal catheter system is advanced and directed under imaging guidance around the circumference of the cardiac valve. One exemplary circumferential trajectory of the cerclage traversal catheter system is around the mitral-valve annulus from the coronary sinus ostium to the origin of the great cardiac vein, and thereafter through non-anatomic spaces (including but not limited to, the mitral annulus, left atrial cavity, right atrial cavity, interatrial septum, and transverse fossa) to return to the coronary sinus ostium. In such an embodiment, the target and capture device 200/300/500 could be positioned so as to guide the cerclage traversal catheter system, e.g. under imaging guidance, as it returns to the coronary sinus ostium.

Figure 7A:
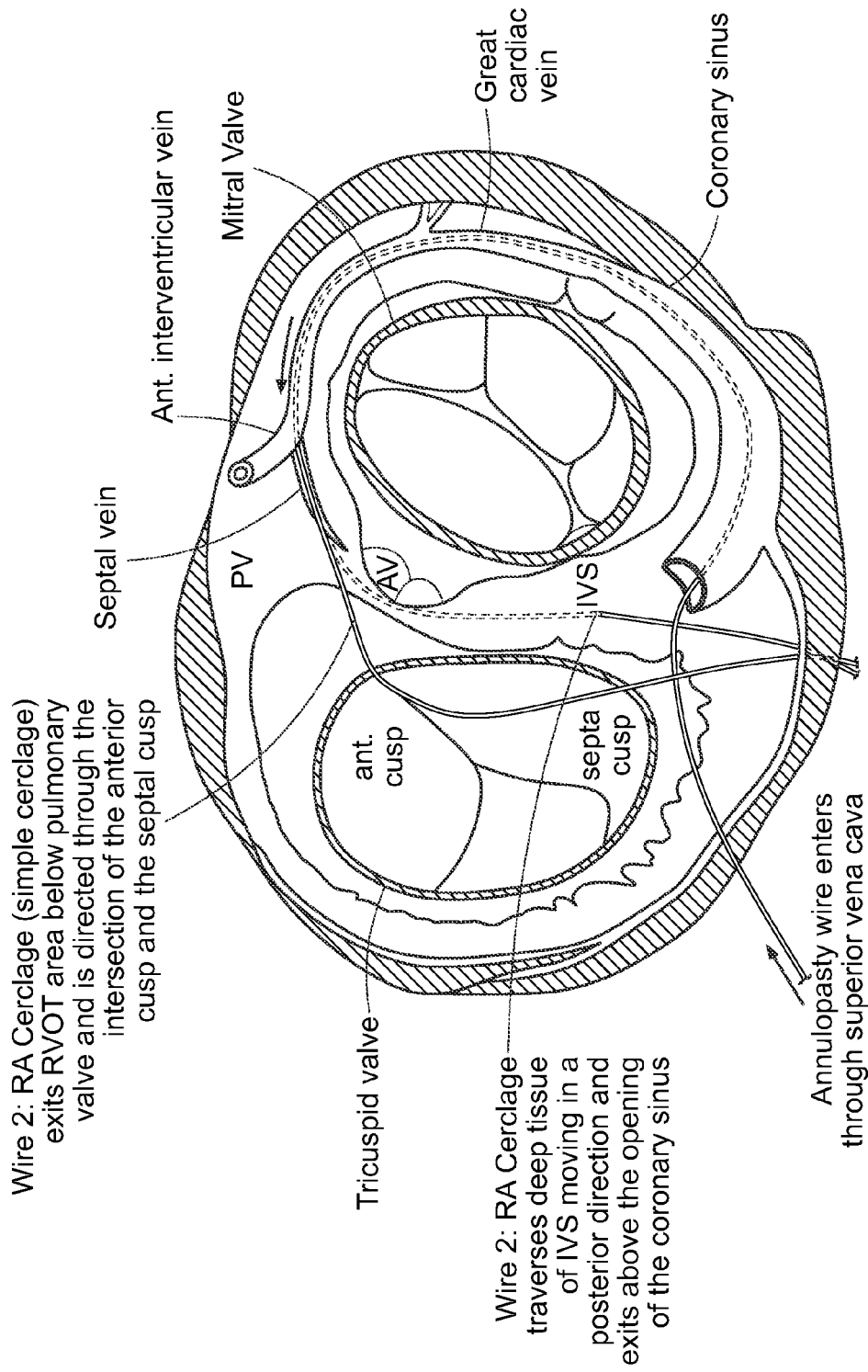
FIG. 7A is a schematic atrial view of a human heart with the atrial tissue removed, taken at the level of the atrioventricular valves, showing in dashed lines two alternative trajectories of the cerclage annuloplasty tensioning element around the mitral valve. Depicted trajectories include "simple" or "right ventricular reentry" cerclage, or alternatively "right atrial" reentry cerclage.
Figure 7B:
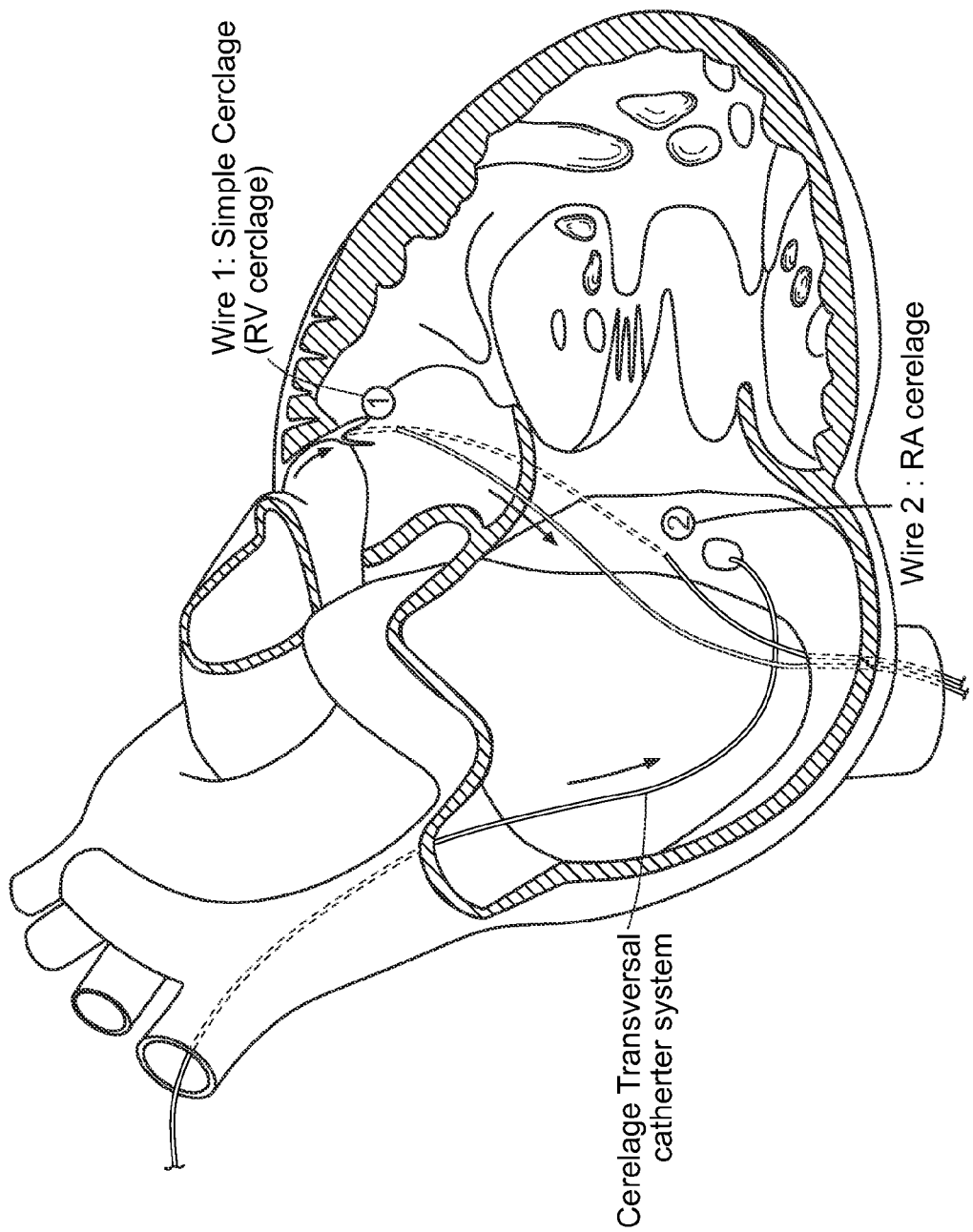
FIG. 7B is a right ventricular perspective view of the heart with portions of the right atrial and right ventricular free walls broken away to show the cerclage traversal reentry sites of FIG. 7A.

Two examples of trajectories are shown in FIGS. 7A and 7B. The first trajectory (labeled a "simple" or "RV" trajectory) is one in which the cerclage traversal catheter system enters the right atrium through the superior vena cava and is then introduced through the coronary ostium into the coronary sinus. The cerclage traversal catheter system is advanced through the great cardiac vein into a basal blood vessel, such as a basal septal perforator vein. The cerclage traversal catheter system then exits the septal perforator vein through myocardial interstitium into the right ventricle, re-entering the right atrium along the septal tricuspid valve commisure (at the intersection of the anterior cusp and the septal cusp). The target and capture device 200/300/500 is suitably positioned at this reentry site and is positioned so as to conform to the reentry site. Suitable counterclockwise torque of the target and capture device 200/300/500 alone or together with the delivery catheter can be applied to maintain apposition of the target and capture device 200/300/500 at the reentry site. The cerclage traversal catheter system is then guided through the reentry site via the target and capture device 200/300/500 which, further, captures or ensnares the cerclage traversal catheter system as it reenters. The cerclage traversal catheter system is then replaced with a tensioning element, such as a tensioning suture. The replacement can occur, for example, by attaching the tensioning material to the cerclage traversal catheter system and advancing the tensioning material along the path of the cerclage traversal catheter system as the cerclage traversal catheter system is withdrawn. In an alternative approach, coronary veins are entered in the opposite direction from the right atrium or right ventricle under imaging guidance into a branch of the coronary sinus.

An alternative or "complex" right atrial cerclage trajectory shown in FIGS. 7A and 7B extends further posterior through the basal septal myocardium into the right atrium near the coronary sinus. The wire traverses deep tissue of the septum moving in a posterior direction and exits above the opening of the coronary sinus. The target and capture device 200/300/500 would also be suitably positioned at this reentry site and is positioned so as to conform to the reentry site. Suitable counterclockwise torque of the target and capture device 200/300/500 alone or together with the delivery catheter can be applied to maintain apposition of the target and capture device 200/300/500 at the reentry site. The cerclage traversal catheter system is then guided through the reentry site via the target and capture device 200/300/500 which, further, captures or ensnares the cerclage traversal catheter system as it reenters.

In yet further embodiments, a permanent magnet or electromagnet is incorporated on the target and capture device 200/300/500 so as to apply a local docking force to aid in capture of a magnetic cerclage traversal catheter system.

Figure 7C:
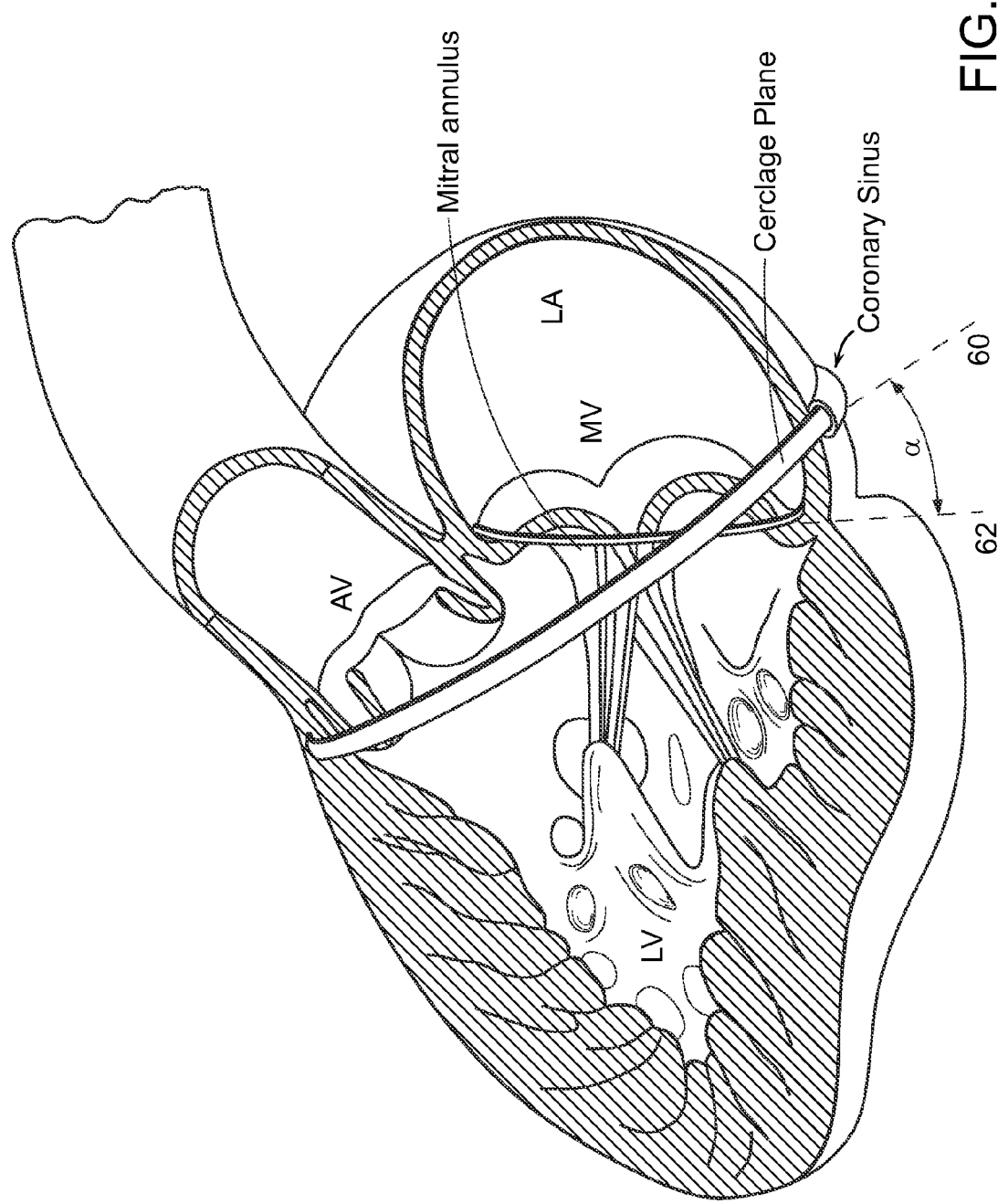
FIG. 7C is a left ventricular view of the heart showing the tilted plane of the coronary sinus cerclage annuloplasty in relation to the plane of the mitral annulus. The drawing schematically illustrates a smaller traditional surgical mitral valve annuloplasty ring over the mitral valve annular plane and the larger coronary artery cerclage in a plane that is tilted to the mitral plane so as to encompass the left ventricular outflow tract. Evident from this diagram is the transmission of leaflet-apposing force during application of cerclage tension, even when the coronary sinus courses along the left atrial free wall far from the mitral valve annulus.
Figure 7D:
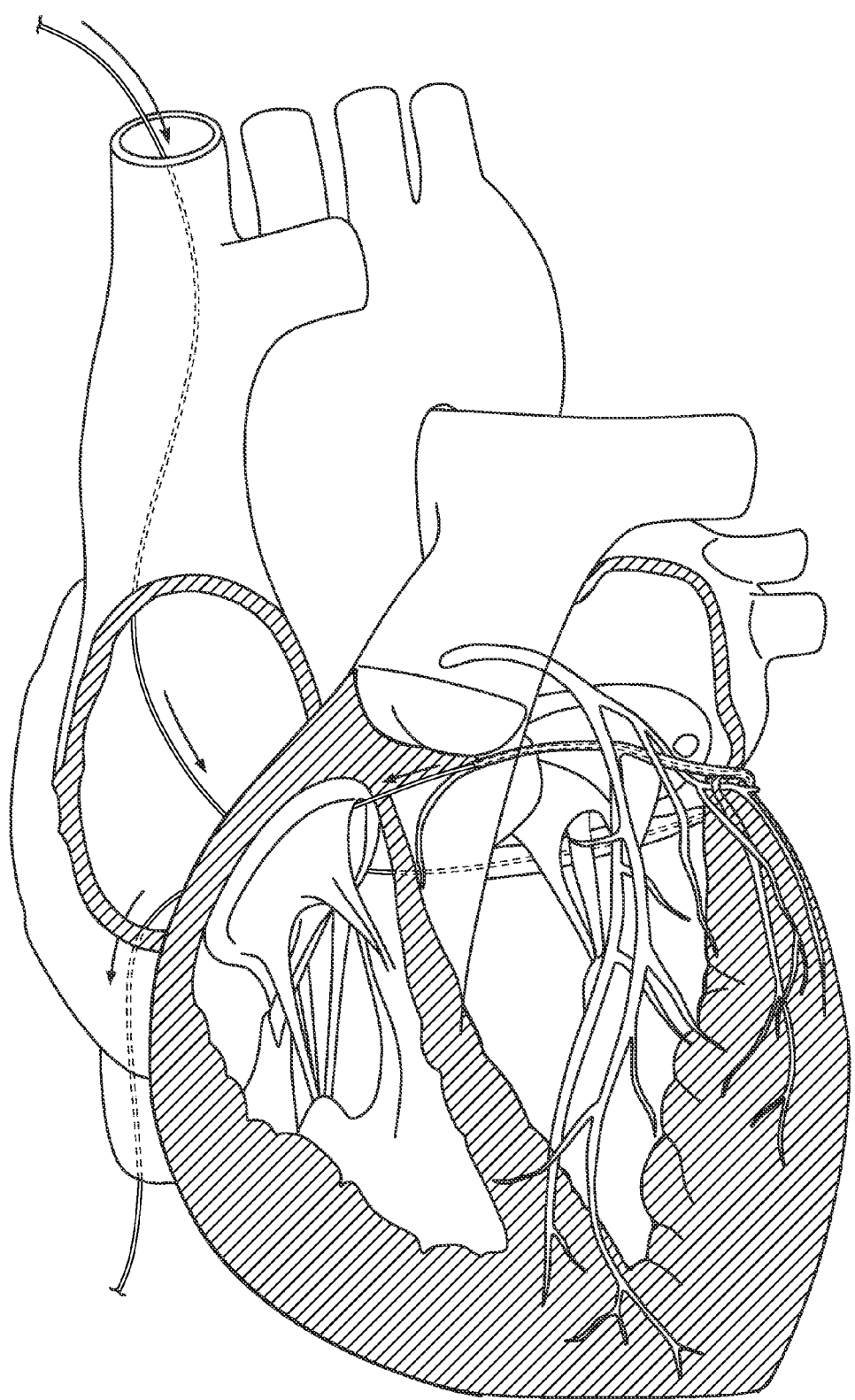
FIG. 7D further shows a perspective view of the heart with the cerclage annuloplasty trajectories of FIG. 7B.
Figure 8A:
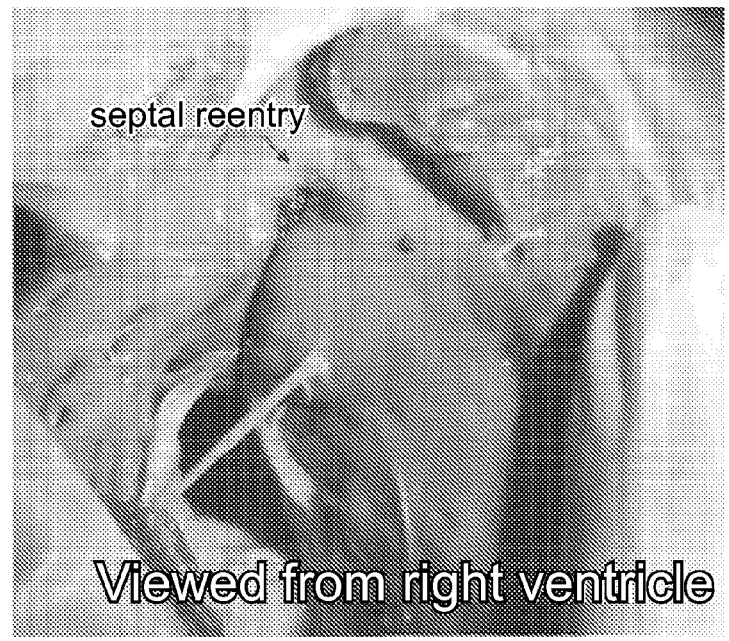
FIGS. 8A-B show the septal reentry sites viewed from the right ventricle in RV cerclage (FIG. 8A) and viewed from the right atrium in RA cerclage (FIG. 8B).
Figure 8B:
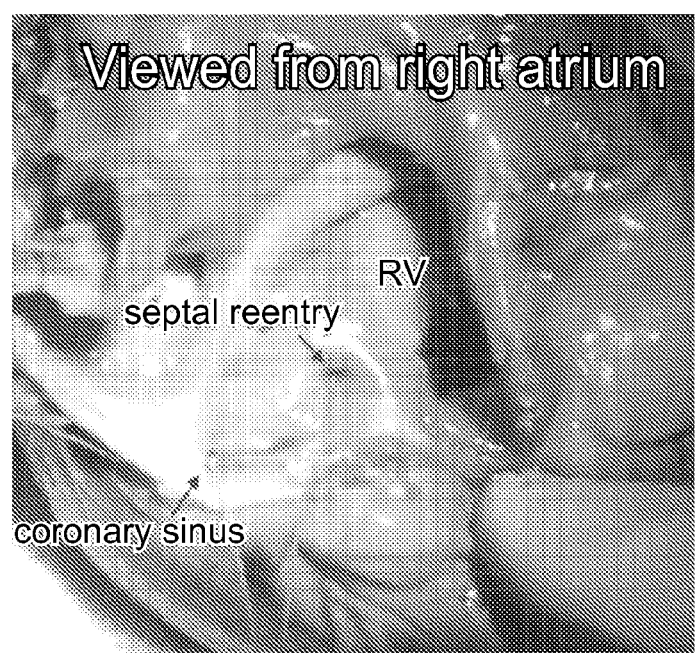

The plane of the resulting cerclage annuloplasty is shown in FIGS. 7C-7D. This plane of cerclage is shown to be related to and in the plane of the coronary sinus 60 such that annuloplasty remains uniquely feasible even if the coronary sinus is remote from the mitral valve annuloplasty. As the figures indicate, the plane of cerclage 60 enhances mitral valve coaptation, even when the coronary sinus is geometrically remote from the mitral valve annulus, because it is "tilted" toward the left ventricular outflow tract. The illustrated angle a between the cerclage plane 60 and the plane of the mitral valve annulus 62 is therefore advantageous. Moreover, the illustrated trajectories of the cerclage annuloplasty induces reciprocal mitral valve coaptation and left ventricular outflow tract relaxation during ventricular systole.

Tension is applied via the annuloplasty cerclage through, for example, tensioning material such as suture material exchanged for the cerclage traversal catheter system. Tension can be applied through both ends of the suture as they are externalized at the point of vascular access. Tension is applied under imaging guidance until the desired degree of mitral annular circumferential reduction is accomplished, or until the mitral valve regurgitation is reduced, or until other deleterious endpoints are achieved such as mitral valve inflow obstruction. Tension is secured, such as by using a knot or using a tension fixation device applied to both ends of the suture at the right atrium or right ventricle where the two cerclage trajectories cross, or at the point of vascular access, or in between the two. Tension is delivered by counterpressure against the fixation device, for example, applied through a delivery catheter. Before fixation, tension can be released or reduced, for example, to reposition the protection device or to achieve a lower degree of mitral annular circumferential reduction.

As tension is applied, valvular regurgitation is assessed repeatedly and non-invasively by an appropriate imaging technique. Such imaging techniques include X-ray angiography, MRI, external or intracavitary or intravascular ultrasound, X-ray computed tomography, pressure transducers in an affected chamber such as the left atrium or the pulmonary vein or the pulmonary artery, or a "fusion" or combination of any of the above. After the valvular regurgitation has been reduced (or even eliminated) and a desired tension is achieved, the tension is fixed. If the resulting circumferential suture is secured to form a closed loop, the suture essentially becomes a cerclage suture. Tension in the suture can also be released (for example, using another secondary catheter, such as a catheter with a suture-release blade) in order to readjust or remove the tension suture.

Having illustrated and described the principles of the invention by several embodiments, it should be apparent that those embodiments can be modified in arrangement and detail without departing from the principles of the invention. Thus, the invention includes all such embodiments and variations thereof, and their equivalents.

What is claimed is:

1. A target and capture device for transcatheter cerclage annuloplasty comprising:
    an expandable and collapsible mesh comprising a plurality of criss-crossing wire-like members that move freely relative to each other and formed of a shaped memory material, the expandable and collapsible mesh configured so as to conform to the curvature of the right ventricle and form a U-shape or J-shape that conforms to the right ventricular outflow tract and/or infundibulum when in its expanded state and configured so as to be insertable through a catheter in a patient's vasculature when collapsed; and
    the expandable and collapsible mesh having an imageable target therein.

2. The target and capture device of claim 1 wherein the mesh is configured so as to displace the valvar chordae and the true and false trabecular muscles against the endocardial border of the right ventricular septum.

3. The target and capture device of claim 1 wherein the mesh is configured to apply pressure on expansion, thereby displacing the valvar chordae and the true and false trabecular muscles toward the endocardial surface.

4. The target and capture device of claim 1 further comprising a push member positioned to expand and collapse the mesh upon inflation and deflation.

5. The target and capture device of claim 1 wherein the mesh comprises a plurality of ring-like wire-like members interwoven along the length of a plurality of horizontal wire-like members.

6. The target and capture device of claim 5 wherein the ring-like elements are moveable along the wires so as to independently vary the size of openings in the mesh.

7. The target and capture device of claim 5, wherein the plurality of ring-like wire-like members include ring that the plurality of horizontal wire-like members pass through.

8. The target and capture device of claim 1 further comprising a unipolar or bipolar electrode set for determining the position of the target and capture device in relation to functional electrophsiological fiducial markers.

9. The target and capture device of claim 8, wherein the unipolar or bipolar electrode set performs a His electrocardiogram.

10. The target and capture device of claim 1, wherein the expandable and collapsible mesh is further configured to capture and/or ensnare a catheter inserted therethrough.

11. The target and capture device of claim 10, wherein the catheter is a cerclage traversal catheter system.

12. The target and capture device of claim 1, wherein the criss-crossing wire-like members are interwoven.

13. A target and capture device for transcatheter cerclage annuloplasty comprising:
an expandable and collapsible mesh comprising a plurality of criss-crossing wire-like members that move freely relative to each other and formed of a shaped memory material, the expandable and collapsible mesh configured so as to form a U-shape or a J-shape when in its expanded state and configured so as to be insertable through a catheter in a patient's vasculature when collapsed; and
the expandable and collapsible mesh having an imageable target therein.

14. The device of claim 13, wherein the expandable and collapsible mesh forms a basket-like U-shape when in its expanded state.

15. The device of claim 13, wherein the expandable and collapsible mesh confirms with the geometry of the right ventricular inflow and the outflow tract along the interventricular septum when in its expanded state.

16. The device of claim 13, wherein the expandable and collapsible mesh conforms to the right ventricular outflow tract and/or infundibulum when in its expanded state.

* * * * *